US012667609B2

(12) United States Patent
Sun

(10) Patent No.: US 12,667,609 B2
(45) Date of Patent: Jun. 30, 2026

(54) **RECOMBINANT FUSION PROTEIN VACCINE CONTAINING *CLOSTRIDIOIDES DIFFICILE* FliC AND FliD**

(71) Applicant: University of South Florida, Tampa, FL (US)

(72) Inventor: Xingmin Sun, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 266 days.

(21) Appl. No.: 18/390,057

(22) Filed: Dec. 20, 2023

(65) Prior Publication Data

US 2024/0261383 A1 Aug. 8, 2024

Related U.S. Application Data

(60) Provisional application No. 63/483,209, filed on Feb. 3, 2023.

(51) Int. Cl.
*A61K 39/08* (2006.01)
*A61K 35/16* (2015.01)
*C07K 14/33* (2006.01)

(52) U.S. Cl.
CPC .............. *A61K 39/08* (2013.01); *A61K 35/16* (2013.01); *C07K 14/33* (2013.01)

(58) Field of Classification Search
None
See application file for complete search history.

(56) References Cited

U.S. PATENT DOCUMENTS

2014/0127215 A1    5/2014  Berry et al.
2016/0250283 A1*   9/2016  Ghose-Paul  ...........  C07K 14/33
                                                          514/2.4
2020/0254082 A1    8/2020  Sun et al.

OTHER PUBLICATIONS

Tao et al, Immune responses induced by a combined vaccination with a recombinant chimera of Mycoplasma hyopneumoniae antigens and capsid virus-like particles of porcine (Year: 2020).*
Postel, S., et al., Bacterial flagellar capping proteins adopt diverse oligomeric states. elife, 2016. 5:e18857.
Tasteyre, A., et al., Role of FliC and FliD Flagellar Proteins of Clostridium difficile in Adherence and Gut Colonization. Infection and Immunity, Dec. 2001. 69(12): p. 7937-7940.
Tasteyre, A., et al., Molecular Characterization of fliD Gene Encoding Flagellar Cap and Its Expression among Clostridium difficile Isolates from Different Serogroups. Journal of Clinical Microbiology, Mar. 2001. 39(3): p. 1178-1183.
Dingle, T.C., et al., Mutagenic Analysis of the Clostridium difficile Flagellar Proteins, FliC and FliD, and Their Contribution to Virulence in Hamsters. Infection and Immunity, Oct. 2011. 79(10): p. 4061-4067.

Ghose, C., et al., Immunogenicity and protective efficacy of recombinant Clostridium difficile flagellar protein FliC. Emerging Microbes and Infections (2016)5, e8.
Karpinski, P., et al., Motility and the genotype diversity of the flagellin genes fliC and fliD among Clostridioides difficile ribotypes. Anaerobe, 73 (2022): 102476.
Tasteyre, A., et al., Phenotypic and Genotypic Diversity of the Flagellin Gene (fliC) among Clostridium difficile Isolates from Different Serogroups. Journal of Clinical Microbiology, Sep. 2000. 38(9): p. 3179-3186.
Stevenson, E., N.P. Minton, and S.A. Kuehne, The role of flagella in Clostridium difficile pathogenicity. Trends in microbiology, 2015. 23(5): p. 275-282.
Yonekura, K., S. Maki-Yonekura, and K. Namba, Structure analysis of the flagellar cap-filament complex by electron cryomicroscopy and single-particle image analysis. Journal of Structural Biology, 2001. 133(2-3): p. 246-253.
Yoshino, Y., et al., Clostridium difficile flagellin stimulates toll-like receptor 5, and toxin B promotes flagellin-induced chemokine production via TLR5. Life Sci, 2013. 92(3): p. 211-7.
Ghose, C., et al., Toll-Like Receptor 5-Dependent Immunogenicity and Protective Efficacy of a Recombinant Fusion Protein Vaccine Containing the Nontoxic Domains of Clostridium difficile Toxins A and B and Salmonella enterica Serovar Typhimurium Flagellin in a Mouse Model of Clostridium difficile Disease. Infection and Immunity, Jun. 2013. 81(6): p. 2190-21966.
Batah, J., et al., Clostridium difficile flagella induce a pro-inflammatory response in intestinal epithelium of mice in cooperation with toxins. Scientific Reports, Jun. 2017. 7:3256.
Jarchum, I., et al., Toll-Like Receptor 5 Stimulation Protects Mice from Acute Clostridium difficile Colitis. Infection and Immunity, Apr. 2011. 79(4): p. 1498-1503.
Trzilova, D., et al., Flagellum and toxin phase variation impacts intestinal colonization and disease development in a mouse model of Clostridioides difficile infection. Gut Microbes, 2022. 14(1), 2038854.
Stabler, R.A., et al., Comparative genome and phenotypic analysis of Clostridium difficile 027 strains provides insight into the evolution of a hypervirulent bacterium. Genome Biology, Sep. 2009. 10(9), Article R102.
Groß, U., et al., Comparative genome and phenotypic analysis of three Clostridioides difficile strains isolated from a single patient provide insight into multiple infection of C. difficile. BMC Genomics, 2018. 19(1): p. 1-14.
He, M., et al., Evolutionary dynamics of Clostridium difficile over short and long time scales. Proceedings of the National Academy of Sciences, Apr. 2010. 107(16): p. 7527-7532.
Tasteyre, A., et al., A Clostridium difficile gene encoding flagellin. Microbiology, 2000. 146: p. 957-966.
Sebaihia, M., et al., The multidrug-resistant human pathogen Clostridium difficile has a highly mobile, mosaic genome. Nature genetics, Jul. 2006. 38(7): p. 779-786.

(Continued)

*Primary Examiner* — Daniel E Kolker
*Assistant Examiner* — Rudolph E. Sloup, Jr. IV
(74) *Attorney, Agent, or Firm* — Michele L. Lawson; Shumaker, Loop & Kendrick, LLP

(57) ABSTRACT

A novel vaccine and methods of preventing and treating *C. difficile* infection in a patient is described. The vaccine is comprised of a fusion protein (denoted FliCD) comprised of the FliC and FliD from *C. difficile* and joined by a linker sequence. Administration of the vaccine, as well as anti-FliCD serum, has been shown to prevent *C. difficile* infection as well as treat existing infections.

2 Claims, 9 Drawing Sheets

Specification includes a Sequence Listing.

(56)          References Cited

OTHER PUBLICATIONS

Cairns, M., et al., Genomic Epidemiology of a Protracted Hospital Outbreak Caused by a Toxin A-Negative Clostridium difficile Sublineage PCR Ribotype 017 Strain in London, England. Journal of Clinical Microbiology, Oct. 2015. 53(10): p. 3141-3147.

Riedel, T., et al., High metabolic versatility of different toxigenic and non-toxigenic Clostridioides difficile isolates. International Journal of Medical Microbiology, Sep. 2017. 307(6): p. 311-320.

Depitre, C., et al., Serogroup F strains of Clostridium difficile produce toxin B but not toxin A. Journal of Medical Microbiology, Jun. 1993. 38(6): p. 434-441.

Soehn, F., et al., Genetic rearrangements in the pathogenicity locus of Clostridium difficile strain 8864—implications for transcription, expression and enzymatic activity of toxins A and B. Molecular and General Genetics, May 1998. 258 (3): p. 222-232.

Janezic, S., et al., Comparative genomics of Clostridioides difficile toxinotypes identifies module-based toxin gene evolution. Microbial Genomics, 2020:6, p. 1-13.

Brouwer, M.S., et al., Draft Genome Sequence of the Nontoxigenic Clostridium difficile Strain CD37. 2012, Journal of Bacteriology, Apr. 2012. p. 2125-2126.

Wang, S., et al., Genomic and Phenotypic Characterization of the Nontoxigenic Clostridioides difficile Strain CCUG37785 and Demonstration of Its Therapeutic Potential for the Prevention of C. difficile Infection. Microbiology Spectrum, Mar./Apr. 2022. 10(2): p. 1-14.

Cartman, S.T., et al., Precise Manipulation of the Clostridium difficile Chromosome Reveals a Lack of Association between the tcdC Genotype and Toxin Production. Applied and Environmental Microbiology, Jul. 2012. 78(13): p. 4683-4690.

Wang, Y.K., et al., A chimeric protein comprising the glucosyltransferase and cysteine proteinase domains of toxin B and the receptor binding domain of toxin A induces protective immunity against Clostridium difficile infection in mice and hamsters. Human Vaccines & Immunotherapeutics, Sep. 2015. 11(9): p. 2215-2222.

Sorg, J.A. and A.L. Sonenshein, Inhibiting the Initiation of Clostridium difficile Spore Germination using Analogs of Chenodeoxycholic Acid, a Bile Acid. Journal of Bacteriology, Oct. 2010. 192(19): p. 4983-4990.

Chen, X., et al., A mouse model of Clostridium difficile-associated disease. Gastroenterology, Dec. 2008. 135(6): p. 1984-1992.

Joshi, L.T., et al., Contribution of Spores to the Ability of Clostridium difficile To Adhere to Surfaces. Applied and Environmental Microbiology, Nov. 2012. 78(21): p. 7671-7679.

* cited by examiner

```
                          SEQUENCE LISTING

Sequence total quantity: 7
SEQ ID NO: 1              moltype = DNA   length = 12
FEATURE                  Location/Qualifiers
source                   1..12
                         mol_type = other DNA
                         organism = synthetic construct
SEQUENCE: 1
ggtggctctg gt                                                        12

SEQ ID NO: 2              moltype = AA   length = 4
FEATURE                  Location/Qualifiers
source                   1..4
                         mol_type = protein
                         organism = synthetic construct
SEQUENCE: 2
GGSG                                                                 4

SEQ ID NO: 3              moltype = AA   length = 319
FEATURE                  Location/Qualifiers
source                   1..319
                         mol_type = protein
                         organism = Clostridioides difficile
SEQUENCE: 3
MSDYINEELI KKIKSRNDKD VNYTKEGKIM RVNTNVSALI ANNQMGRNVN AQSKSMEKLS    60
SGVRIKRAAD DAAGLAISEK MRAQIKGLDQ AGRNVQDGIS VVQTAEGALE ETGNILQRMR    120
TLSVQSSNET NTAEERQKIA DELLQLKDEV ERISSSIEFN GKKLLDGSST EIRLQVGANF    180
GTNVAGTTNN NNEIKVALVN TSSIMSKAGI TSSTIASLNA DGTSGTDAAK QMVSSLDVAL    240
KELNTSRAKL GAQQNRLEST QNNLNNTIEN VTAAESRIRD TDVASEMVNL SKMNILVQAS    300
QSMLAQANQQ PQGVLQLLG                                                 319

SEQ ID NO: 4              moltype = DNA   length = 960
FEATURE                  Location/Qualifiers
source                   1..960
                         mol_type = genomic DNA
                         organism = Clostridioides difficile
SEQUENCE: 4
atgtccgatt atataaatga agaattaata aaaaagatta aaagtagaaa tgacaaggat    60
gtcaactata ctaaggaggg taaaataatg agagttaata caaatgtaag tgctttgata    120
gcaaataacc aaatgggaag aaacgtaaat gcacaaagta agtctatgga gaagttatct    180
tctggtgtta gaattaagag agctgctgat gatgctgctg ggcttgctat atctgagaaa    240
atgagagctc aaataaaagg tttagaccaa gcaggaagaa acgttcaaga tggtatatct    300
gttgcacaaa cagcagaagg tgcattagaa gaaactggta atatactaca aagaatgaga    360
actttatcag tacaatcttc aaatgaaact aatactgctg aagaaagaca aaagatagct    420
gatgagttgt tacaattaaa ggatgaagtt gaaagaatat caagctcaat tgagtttaat    480
ggtaagaaat tacttgatgg aagttctaca gaaataagat tacaagttgg agctaatttt    540
ggaacaaatg ttgcaggaac aactaacaac aacaatgaaa taaaagttgc tctagtaaat    600
acttcaagta taatgagtaa agcaggtata acaagttcta caatagcaag cttaaatgca    660
gatggaactt ctggaacaga tgcagctaaa caaatggtgt ctagcttaga tgtagctctt    720
aaagaattaa atacatcaag agcaaaatta ggggcacaac aaaatagact agaatcaact    780
caaaacaact taaataatac tatagaaaat gttacagcag ctgaatcaag aataagagat    840
acagatgttg cttcagaaat ggttaactta tctaaaatga atatattagt tcaagcatca    900
cagtcaatgc ttgctcaagc taatcagcaa ccacaaggag ttttacaatt attaggataa    960

SEQ ID NO: 5              moltype = AA   length = 507
FEATURE                  Location/Qualifiers
source                   1..507
                         mol_type = protein
                         organism = Clostridioides difficile
SEQUENCE: 5
MSSISPIRVT GLSGNFDMEG IIEASMIRDK EKVDKAKQEQ QIVKWKQEIY RNVIQESKDL    60
YDKYLSVNSP NSIVSEKAYS STRITSSDES IIVAKGSAGA EKINYQFAVS QMAEPAKFTI    120
KLNSSEPIVR QFPPNASGAS SLTIGDVNIP ISEQDTTSTI VSKINSLCAD NDIKASYSEM    180
TGELIISRKQ TGSSSDINLK VIGNDNLAQQ IANDNGITFA NDASGNKVAS VYGKNLEADV    240
TDEHGRVTHI SKEQNSFNID NIDYNVNSKG TAKLTSVTDT EEAVKNMQAF VDDYNKLMDK    300
VYGLVTTKKP KDYPPLTDAQ KEDMTTEEIE KWEKKAKEGI LRNDDELRGF VEDIQSAFFG    360
DGKNIIALRK LGINESENYN KKGQISFNAD TFSKALIDDS DKVYKTLAGY SSNYDDKGMF    420
EKLKDIVYEY SGSSTSKLPK KAGIEKTASA SENVYSKQIA EQERNISRLV EKMNDKEKRL    480
YAKYSALESL LNQYSSQMNY FSQAQGN                                        507

SEQ ID NO: 6              moltype = DNA   length = 1524
FEATURE                  Location/Qualifiers
source                   1..1524
                         mol_type = genomic DNA
```

-continued

```
                        organism = Clostridioides difficile
SEQUENCE: 6
atgtcaagta taagtcctat aagagttaca ggtctttcag gaaattttga tatggaaggc  60
ataatcgaag ctagtatgat tagagacaag gaaaaagttg ataaagcaaa acaagaacaa  120
caaatcgtta aatggaagca agaaatatat agaaatgtta tacaagaatc aaaagatctt  180
tatgataaat atctaagcgt aaattctcct aatagtatag taagtgaaaa agcatactct  240
tctacaagaa taaccagttc tgatgaaagt attatagtag caaaaggctc agctggtgca  300
gaaaaaataa attatcaatt tgcagtttct caaatggctg aaccagcaaa atttactatt  360
aaattaaatt caagtgaacc tattgttcga cagttccctc caaatgccag tggagctagt  420
tctttaacta taggagatgt aaatatacca atatctgaac aagatactac aagtactatt  480
gtaagtaaga taaactccct ttgcgcagat aatgatataa aggcttctta tagtgagatg  540
acaggtgaat tgattatttc gagaaaacaa actggttcgt catcagacat taatttaaaa  600
gtaattggaa atgacaattt agctcagcaa attgctaatg ataatggtat cacatttgca  660
aatgatgcta gtgtggaaacaa agtggcaagt gtatatggaa aaatctaga agctgatgta  720
actgatgaac atggaagagt aactcatata agtaaagaac aaaattcatt taatatagat  780
aatattgact ataatgtaaa ttcaaaagga actgcaaagt tgacttctgt cactgatact  840
gaagaagctg ttaaaaatat gcaagcattt gtggatgatt ataataaact gatggacaag  900
gtctatggtt tagttactac taaaaaacca aaagattatc cgcctcttac agatgcccaa  960
aaagaagata tgacaactga agaaatagaa aaatgggaaa agaaagctaa agaaggtata  1020
cttagaaatg atgatgagtt aagaggtttt gttgaagata ttcagtctgc atttttttgga  1080
gatggaaaaa atattattgc attaagaaaa ctaggtatca atgaaagcga aaattacaat  1140
aaaaaaggtc aaatatcatt taatgcagat actttttcaa aggctcttat agatgatagt  1200
gataaggtat acaaaacact agcaggttat tcttcgaatt atgatgataa gggaatgttt  1260
gaaaagctaa aagatattgt atatgaatat tctggaagtt caacttctaa acttcctaaa  1320
aaagcaggta tagaaaaaac tgcttctgct agtgaaaatg tatattcaaa acaaattgca  1380
gagcaagaaa gaaatataag caggttagtt gaaaaaatga atgataaaga gaaaagactt  1440
tatgctaaat attcagcctt agaatctttg ttgaatcagt attcttccca aatgaattat  1500
ttctcacaag cacagggtaa ttaa                                          1524

SEQ ID NO: 7           moltype = AA   length = 830
FEATURE                Location/Qualifiers
source                 1..830
                       mol_type = protein
                       organism = synthetic construct
SEQUENCE: 7
MSDYINEELI KKIKSRNDKD VNYTKEGKIM RVNTNVSALI ANNQMGRNVN AQSKSMEKLS  60
SGVRIKRAAD DAAGLAISEK MRAQIKGLDQ AGRNVQDGIS VVQTAEGALE ETGNILQRMR  120
TLSVQSSNET NTAEERQKIA DELLQLKDEV ERISSSIEFN GKKLLDGSST EIRLQVGANF  180
GTNVAGTTNN NNEIKVALVN TSSIMSKAGI TSSTIASLNA DGTSGTDAAK QMVSSLDVAL  240
KELNTSRAKL GAQQNRLEST QNNLNNTIEN VTAAESRIRD TDVASEMVNL SKMNILVQAS  300
QSMLAQANQQ PQGVLQLLGG GSGMSSISPI RVTGLSGNFD MEGIIEASMI RDKEKVDKAK  360
QEQQIVKWKQ EIYRNVIQES KDLYDKYLSV NSPNSIVSEK AYSSTRITSS DESIIVAKGS  420
AGAEKINYQF AVSQMAEPAK FTIKLNSSEP IVRQFPPNAS GASSLTIGDV NIPISEQDTT  480
STIVSKINSL CADNDIKASY SEMTGELIIS RKQTGSSSDI NLKVIGNDNL AQQIANDNGI  540
TFANDASGNK VASVYGKNLE ADVTDEHGRV THISKEQNSF NIDNIDYNVN SKGTAKLTSV  600
TDTEEAVKNM QAFVDDYNKL MDKVYGLVTT KKPKDYPPLT DAQKEDMTTE EIEKWEKKAK  660
EGILRNDDEL RGFVEDIQSA FFGDGKNIIA LRKLGINESE NYNKKGQISF NADTFSKALI  720
DDSDKVYKTL AGYSSNYDDK GMFEKLKDIV YEYSGSSTSK LPKKAGIEKT ASASENVYSK  780
QIAEQERNIS RLVEKMNDKE KRLYAKYSAL ESLLNQYSSQ MNYFSQAQGN            830
```

RECOMBINANT FUSION PROTEIN VACCINE CONTAINING *CLOSTRIDIOIDES DIFFICILE* FliC AND FliD

CROSS REFERENCE TO RELATED APPLICATIONS

This application is a nonprovisional of and claims priority to U.S. Provisional Patent Application Ser. No. 63/483,209, entitled "Recombinant Fusion Protein Vaccine Containing *Clostridioides* FliC and FliD Protects Mice Against *C. difficile* Infection", filed Feb. 3, 2023, the contents of which are hereby incorporated by reference into this disclosure.

GOVERNMENT SUPPORT

This invention was made with Government support under Grant Nos. R01-AI1132711 and R21-AI113470, awarded by the National Institute of Health. The Government has certain rights in the invention.

FIELD OF INVENTION

This invention relates to treatment and/or prevention of *C. difficile* infection. Specifically, the invention provides a novel recombinant fusion protein vaccine and associated method of preventing and/or treating a bacterial infection such as *C. difficile*.

BACKGROUND OF THE INVENTION

*Clostridioides difficile* (*C. difficile*) is an anaerobic, spore-forming, Gram-positive bacterium, and it is the leading cause of antibiotic-associated diarrhea and colitisi[1,2]. *C. difficile* produces three protein toxins including toxin A (TcdA), toxin B (TcdB), and binary toxin (CDT). The first two are the major virulence factors of *C. difficile* that cause *C. difficile* infection (CDI) symptoms[3,4]. CDI is spread by bacterial spores that are found in the feces, and infections occur in all areas of the world[5,6]. In the United States, there is an occurrence of 8.3 cases per 10,000 patient-days, suggesting that CDI is associated with a large burden on the healthcare system[7]. Currently, very few antibiotics are available for the treatment of CDI, and none of them are fully effective[8]. Antibiotic treatment is often followed by recurrent infection, which leads to the use of nontraditional therapies[9-10].

The flagella of most pathogens increase the occurrence of interactions between the pathogen and the epithelial mucosal surface by facilitating bacteria to chemotaxis toward specific signals. Moreover, bacterial flagella are involved in infection through their roles in host cell adhesion, cell invasion, auto-agglutination, colonization, the formation of biofilms, and the regulation and secretion of non-flagellar bacterial proteins that are involved in the virulence process[11]. *C. difficile* flagellin FliC is the major structural component of the flagellar filament, and the assembly of a flagellum requires other proteins, which are called hook-associated proteins (HAP1, HAP2, and HAP3). The fliD gene encodes the structural component HAP2 of the flagellar cap at the distal end of the filament[12-14]. Both the FliC and FliD proteins are implicated in the attachment of *C. difficile* to the mucus layer of the intestine[15]. Researchers also found that flagellated, motile *C. difficile* adheres more efficiently to the epithelium cell wall of axenic mice than do non-flagellated strains of the same serogroup[16]. Interestingly, a different study showed that both fliC and fliD mutant strains adhered better than did the wild-type 630Δerm strain to human intestine-derived Caco-2 cells, and they were more virulent in hamsters[17]. These conflicting reports suggest a complex role for flagella in CDI.

Given the lack of efficacy in current vaccines against *C. difficile*, what is needed is an efficacious vaccine against *C. difficile* infection (CDI).

SUMMARY OF INVENTION

Bacterial flagella are involved in infection through their roles in host-cell adhesion, cell invasion, auto-agglutination, colonization, the formation of biofilms, and the regulation and secretion of non-flagellar bacterial proteins that are involved in the virulence process. The inventors constructed a fusion protein vaccine (FliCD) containing *Clostridiodes difficile* flagellar proteins FliC and FliD. The immunization of mice with FliCD induced potent IgG and IgA antibody responses against FliCD, protected mice against *C. difficile* infection (GDI), and decreased the *C. difficile* spore and toxin levels in the feces after infection. Additionally, anti-FliCD serum inhibited the binding of *C. difficile* vegetative cells to HCT8 cells. These results show that FliCD fusion protein is an effective vaccine candidate against *C. difficile* infection (CDI).

In an embodiment, a fusion protein is presented comprising: a portion of at least one flagellin protein (FliC) from a Gram-positive bacterium and a portion of at least one cap protein (FliD) from a Gram-positive bacterium, wherein the Gram-positive bacterium is from the genus *Clostridioides*. The Gram-positive bacterium may be *Clostridioides difficile* (*C. difficile*). The portion of the FliC and the FliD may be linked by a linker having sequence SEQ ID NO: 1 or SEQ ID NO: 2. The portion of the FliC may have a sequence of SEQ ID NO: 3 or a sequence having homology thereto. The portion of the FliD may have a sequence of SEQ ID NO: 5 or a sequence having homology thereto. The fusion protein may have a sequence of SEQ ID NO: 7 or a sequence having homology thereto.

In another embodiment, a method of preventing a *C. difficile* infection (CDI) in a patient in need thereof is presented comprising administering to the patient a therapeutically effective amount of a therapeutic agent, the therapeutic agent comprising a serum containing antibodies to at least one flagellin protein from *C. difficile* or a vaccine, the vaccine comprising a fusion protein comprising a portion of at least one flagellin protein (FliC) from *C. difficile* and a portion of at least one cap protein (FliD) from *C. difficile* and a pharmaceutically acceptable carrier, wherein the administration of the serum or the vaccine to the patient prevents CDI. In some embodiments the therapeutic agent may be the serum. The serum may be anti-FliCD serum. In some embodiments, the therapeutic agent may be the vaccine. In the vaccine, the portion of the FliC and the FliD may be linked by a linker having sequence SEQ ID NO: 1 or SEQ ID NO: 2. The portion of the FliC may have a sequence of SEQ ID NO: 3 or a sequence having homology thereto. The portion of the FliD may have a sequence of SEQ ID NO: 5 or a sequence having homology thereto. The fusion protein may have a sequence of SEQ ID NO: 7 or a sequence having homology thereto.

In a further embodiment, a method of treating a *C. difficile* infection (CDI) in a patient in need thereof is presented comprising administering to the patient a therapeutically effective amount of a therapeutic agent selected from the group consisting of serum containing antibodies to at least one flagellin protein from *C. difficile* or a fusion protein composition. The fusion protein composition may comprise: a fusion protein comprising a portion of at least one flagellin protein (FliC) from *C. difficile* and a portion of at least one cap protein (FliD) from *C. difficile*; and a pharmaceutically acceptable carrier, wherein the administration of the therapeutic agent to the patient reduces symptoms of CDI. In some embodiments the therapeutic agent may be the serum. The serum may be anti-FliCD serum. In some embodiments, the therapeutic agent may be the vaccine. In the vaccine, the portion of the FliC and the FliD may be linked by a linker having sequence SEQ ID NO: 1 or SEQ ID NO: 2. The portion of the FliC may have a sequence of SEQ ID NO: 3 or a sequence having homology thereto. The portion of the FliD may have a sequence of SEQ ID NO: 5 or a sequence having homology thereto. The fusion protein may have a sequence of SEQ ID NO: 7 or a sequence having homology thereto.

In a further embodiment a kit for preventing and/or treating CDI is presented comprising a fusion protein comprising at least a portion of a first flagellin protein and at least a portion of a second flagellin protein and a pharmaceutically acceptable carrier. Instructions for use may also be included in the kit. The first flagellin protein may be at least a portion of FliC and the second flagellin protein may be at least a portion of FliD from *C. difficile*. The FliC may have the sequence of SEQ ID NO: 3, or a sequence having homology thereto, encoded by SEQ ID NO: 4 or a sequence having homology thereto. The FliD may have the sequence of SEQ ID NO: 5, or a sequence having homology thereto, encoded by SEQ ID NO: 6 or a sequence having homology thereto. A linker may be used to connect the first and second flagellin proteins. The linker may have the sequence of SEQ ID NO: 1 encoding SEQ ID NO: 2. The fusion protein may have the sequence of SEQ ID NO: 7 or a sequence having homology thereto.

In other embodiments, the kit for preventing and/or treating CDI is comprised of serum containing antibodies to at least one flagellin protein from *C. difficile*. The serum may be anti-FliCD serum. A pharmaceutically acceptable carrier may also be present with the serum and instructions may be included in the kit.

In further embodiments, the kit may contain both the fusion protein composition and the serum containing antibodies as described above.

In a further embodiment, a method of inducing an immune response in a patient having a bacterial infection is presented comprising administering to the patient a therapeutically effective amount of a therapeutic agent selected from the group consisting of a serum containing antibodies to at least one flagellin protein from *C. difficile* or a fusion protein composition, wherein the administration of the therapeutic agent induces increases IgG and/or IgA levels as compared to a control. The fusion protein composition may comprise: a fusion protein comprising a portion of at least one flagellin protein (FliC) from *C. difficile* and a portion of at least one cap protein (FliD) from *C. difficile*; and a pharmaceutically acceptable carrier, wherein the administration of the therapeutic agent to the patient reduces symptoms of CDI. In some embodiments the therapeutic agent may be the serum. The serum may be anti-FliCD serum. In some embodiments, the therapeutic agent may be the vaccine. In the vaccine, the portion of the FliC and the FliD may be linked by a linker having sequence SEQ ID NO: 1 or SEQ ID NO: 2. The portion of the FliC may have a sequence of SEQ ID NO: 3 or a sequence having homology thereto. The portion of the FliD may have a sequence of SEQ ID NO: 5 or a sequence having homology thereto. The fusion protein may have a sequence of SEQ ID NO: 7 or a sequence having homology thereto.

In a further embodiment, a method of inhibiting adhesion of the adhesion of *C. difficile* to intestinal cells of a patient in need thereof is presented comprising administering to the patient a therapeutically effective amount of a therapeutic agent selected from the group consisting of a serum containing antibodies to at least one flagellin protein from *C. difficile* or a fusion protein composition. The fusion protein composition may comprise: a fusion protein comprising a portion of at least one flagellin protein (FliC) from *C. difficile* and a portion of at least one cap protein (FliD) from *C. difficile*; and a pharmaceutically acceptable carrier, wherein the administration of the therapeutic agent to the patient reduces symptoms of CDI. In some embodiments the therapeutic agent may be the serum. The serum may be anti-FliCD serum. In some embodiments, the therapeutic agent may be the vaccine. In the vaccine, the portion of the FliC and the FliD may be linked by a linker having sequence SEQ ID NO: 1 or SEQ ID NO: 2. The portion of the FliC may have a sequence of SEQ ID NO: 3 or a sequence having homology thereto. The portion of the FliD may have a sequence of SEQ ID NO: 5 or a sequence having homology thereto. The fusion protein may have a sequence of SEQ ID NO: 7 or a sequence having homology thereto.

In a further embodiment, a method of decreasing the number of *C. difficile* spores and/or toxin levels in a patient in need thereof is presented comprising administering to the patient a therapeutically effective amount of a therapeutic agent selected from the group consisting of a serum containing antibodies to at least one flagellin protein from *C. difficile* or a fusion protein composition. The fusion protein composition may comprise: a fusion protein comprising a portion of at least one flagellin protein (FliC) from *C. difficile* and a portion of at least one cap protein (FliD) from *C. difficile*; and a pharmaceutically acceptable carrier, wherein the administration of the therapeutic agent to the patient reduces symptoms of CDI. In some embodiments the therapeutic agent may be the serum. The serum may be anti-FliCD serum. In some embodiments, the therapeutic agent may be the vaccine. In the vaccine, the portion of the FliC and the FliD may be linked by a linker having sequence SEQ ID NO: 1 or SEQ ID NO: 2. The portion of the FliC may have a sequence of SEQ ID NO: 3 or a sequence having homology thereto. The portion of the FliD may have a sequence of SEQ ID NO: 5 or a sequence having homology thereto. The fusion protein may have a sequence of SEQ ID NO: 7 or a sequence having homology thereto.

In some embodiments, the homology of the sequences is at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
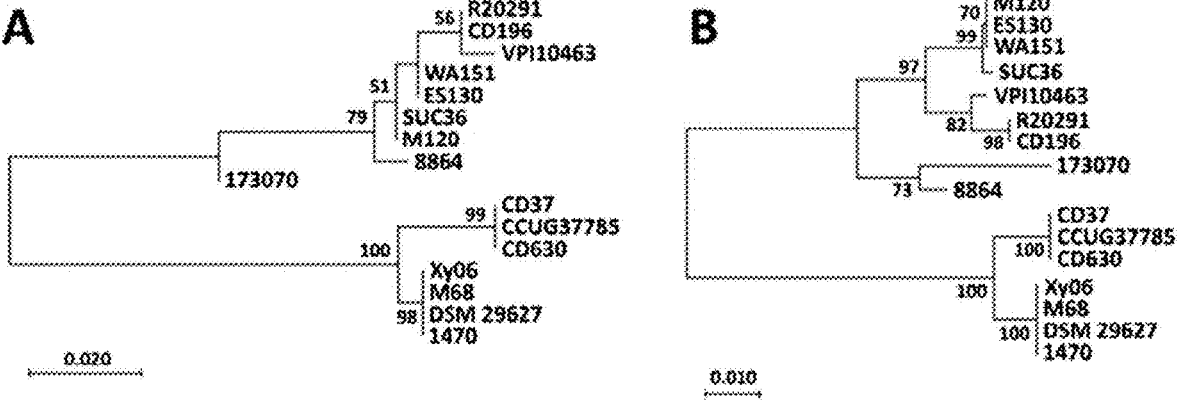
FIG. 1A-B is a series of images depicting FliC and FliD phylogeny. The amino acid sequences of FliC (A) and FliD (B) were aligned with the Muscle algorithm in MegaX before the computation of a Maximum Likelihood tree with 500 bootstrap replicates (bootstrap values >50 displayed). Scale bars indicate 0.020 and 0.010 substitutions per site for FliC and FliD, respectively.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

As used herein, the singular forms "a," "an" and "the" include plural referents unless the context clearly dictates otherwise. For example, "a bacterium" includes "bacteria" or "plurality of bacteria".

As used in this specification and the appended claims, the term "or" is generally employed in its sense including "and/or" unless the context clearly dictates otherwise.

All numerical designations, such as pH, temperature, time, concentration, and molecular weight, including ranges, are approximations which are varied up or down by increments of 1.0, 0.1, 0.01 or 0.001 as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used herein, the term "comprising" is intended to mean that the products, compositions, and methods include the referenced components or steps, but not excluding others. "Consisting essentially of" when used to define products, compositions, and methods, shall mean excluding other components or steps of any essential significance that affect the novel characteristics of the invention as described herein. Thus, a composition consisting essentially of the recited components would not exclude trace contaminants and pharmaceutically acceptable carriers. "Consisting of" shall mean excluding more than trace elements of other components or steps.

As used herein, "about" means approximately or nearly and in the context of a numerical value or range set forth means±10% of the numerical.

As used herein "patient" is used to describe a mammal, preferably a human, to whom treatment is administered, including prophylactic treatment with the compositions of the present invention. Non-limiting examples of mammals include humans, rodents, aquatic mammals, domestic animals such as dogs and cats, farm animals such as sheep, pigs, cows and horses. "Patient" and "subject" are used interchangeably herein.

"Administering" or "administration" as used herein refers to the process by which the compositions of the present invention are delivered to the patient. The compositions may be administered in various ways, including but not limited to, enteral and parenteral routes, namely, orally, rectally, nasally, subcutaneously, intravenously, intraperitoneally, intradermally, and intramuscularly, although other enteral and parenteral routes are contemplated including through the mucosa.

"Parenteral administration" as used herein refers to modes of administration other than enteral and topical administration, usually by injection, and includes, but is not limited to, intravenous, intramuscular, intraarterial, intrathecal, intracapsular, intraorbital, intracardiac, intradermal, intraperitoneal, transtracheal, subcutaneous, subcuticular, intra-articular, subcapsular, intrathecal, intraventricular, intracisternal, intranigral, subarachnoid, intraspinal, and intrasternal injection and infusion. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

"therapeutic agent" as used herein refers to a substance, composition, compound, chemical, component or extract that has measurable specified or selective physiological activity when administered to an individual in a therapeutically effective amount. In some embodiments, the therapeutic agent may be an antibacterial composition. Examples of therapeutic agents as used in the present invention include, but are not limited to, fusion proteins. At least one therapeutic agent is used in the compositions of the present invention, however in some embodiments, multiple therapeutic agents are used. In some embodiments, the novel recombinant fusion protein described herein may be combined with another therapeutic agent that targets a different area of the bacteria or targets a different disease target. In some embodiments, one or more therapeutic agents may be encapsulated within a nanoparticle. In some embodiments, the therapeutic agent is used to treat an infection such as a bacterial infection like that from a Gram positive bacteria like *C. difficile*.

The terms "reduce or inhibit" as used herein refers to the ability to cause an overall decrease of 10%, 20%, 30%, 40%, 50%, 60%, 70%, 75%, 80%, 85%, 90%, 95%, or greater. Reduce or inhibit can refer, for example, to the symptoms of the disorder being treated or the presence, growth, adhesion, or spread of bacteria.

A "vaccine" as used herein refers to an antigenic composition usually comprising an infectious factor or a portion of an infectious factor, such as an antigen, in combination with an immune adjuvant, administered into the body to elicit an immune response. The antigenic portion may be a microorganism, such as a virus or bacterium, or a portion thereof; a natural product purified from a microorganism, or a portion thereof; or a synthetic or genetically engineered protein, peptide, polysaccharide, or similar product, or a portion thereof. In some embodiments, the antigenic portion of the vaccine of the present invention is comprised of a fusion protein constructed from the FliC and FliD of *C. difficile*.

A "fusion protein" or "fusion peptide" as used herein refers to a protein generated from at least two similar or distinct components (e.g., at least a portion of a flagellin, at least a portion of an antigen, at least a portion of a bacterial protein such as *C. difficile*) that are linked covalently or noncovalently. The components of the fusion protein can be made, for example, synthetically or by recombinant nucleic acid techniques (e.g., transfection of a host cell with a nucleic acid sequence encoding a component of the fusion protein, such as at least a portion of an antigen or a bacterial protein). One component of the fusion protein (e.g., at least a portion of a flagellin protein, at least a portion of an antigen, at least a portion of a bacterial protein such as *C. difficile*) can be linked to another component of the fusion protein (e.g., at least a portion of a flagellin protein, at least a portion of an antigen, at least a portion of a bacterial protein such as *C. difficile*) using chemical conjugation techniques, including peptide conjugation, or using molecular biological techniques, including recombinant technology, such as the generation of a fusion protein construct. Chemical conjugation (also referred to herein as "chemical coupling") can include conjugation by a reactive group, such as a thiol group (e.g., a cysteine residue) or by derivatization of a primary (e.g., an amino-terminal) or secondary (e.g., lysine) group. In some embodiments, the fusion protein is comprised of at least a portion of FliC and FliD from *C. difficile* and homologues thereof. In some embodiments, the fusion protein is denoted FliCD having homology to SEQ ID NO: 7.

The fusion proteins of the invention can further include a linker between at least one component of the fusion protein (e.g., at least a portion of a flagellin such as FliC, at least a portion of an antigen, at least a portion of a bacterial protein such as *C. difficile*) and at least one other component of the fusion protein (e.g., at least a portion of a flagellin such as FliD, at least a portion of an antigen, at least a portion of a bacterial protein such as *C. difficile*) of the composition, a linker between at least two of similar components of the fusion protein (e.g., at least a portion of a flagellin, at least a portion of an antigen, at least a portion of a bacterial protein such as *C. difficile*) or any combination thereof.

"Linker," as used herein in reference to a fusion protein of the invention, refers to a connector between components of the fusion protein. For example, one component of the fusion protein (e.g., at least a portion of a flagellin such as FliC, at least a portion of an antigen, at least a portion of a bacterial protein such as *C. difficile*) can be linked to a distinct component (e.g., at least a portion of a flagellin such as FliD, at least a portion of an antigen, at least a portion of a bacterial protein such as *C. difficile*) of the fusion protein. Likewise, at least two or more similar or like components of the fusion protein can be linked (e.g., two flagellins can further include a linker between each flagellin, or two antigens can further include a linker between each antigen, or two bacterial proteins can further include a linker between each bacterial protein).

A "therapeutically effective amount" as used herein is defined as concentrations or amounts of components which are sufficient to effect beneficial or desired clinical results, including, but not limited to, any one or more of treating symptoms of bacterial infections, particularly *C. difficile* infection and preventing bacterial infection, particularly *C. difficile* infection. Compositions of the present invention can be used to effect a favorable change in the condition whether that change is an improvement, such as stopping, reversing, or reducing *C. difficile* infection, or a complete elimination of symptoms due to *C. difficile* infection. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of the animal and the route of administration. The dose may be adjusted according to response.

The dosing of compounds and compositions to obtain a therapeutic or prophylactic effect is determined by the circumstances of the patient, as is known in the art. The dosing of a patient herein may be accomplished through individual or unit doses of the compounds or compositions herein or by a combined or prepackaged or pre-formulated dose of a compounds or compositions.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequently. Administration can also be continuous and adjusted to maintaining a level of the compound within any desired and specified range.

The administration of the composition can be extended over an extended period of time, such as from about a week or shorter up to about a year or longer. For example, the dosing regimen can be extended over a period of any of about 2, 3, 4, 5, 6, 7, 8, 9, 10, 11, and 12 months. In some embodiments, there is no break in the dosing schedule. In some embodiments, the interval between each administration is no more than about a week.

The compounds used in the present invention may be administered individually, or in combination with or concurrently with one or more other compounds used against bacteria, including Gram-positive bacteria such as *C. difficile*. Additionally, compounds used in the present invention may be administered in combination with or concurrently with other therapeutics for bacterial infections.

"Prevention" or "preventing" or "prophylactic treatment" as used herein refers to any of: halting the effects of bacterial infection, reducing the effects of bacterial infection, reducing the incidence of bacterial infection, reducing the development of bacterial infection, delaying the onset of symptoms of bacterial infection, increasing the time to onset of symptoms of bacterial infection, and reducing the risk of development of bacterial infection. In some embodiments, the bacterial infection is *C. difficile*.

"Treatment" or "treating" as used herein refers to any of the alleviation, amelioration, elimination and/or stabilization of a symptom, as well as delay in progression of a symptom of a particular disorder. For example, "treatment" of bacterial infection may include any one or more of the following: amelioration and/or elimination of one or more symptoms associated with bacterial infection, reduction of one or more symptoms of bacterial infection, stabilization of symptoms of bacterial infection, and delay in progression of one or more symptoms of bacterial infection. In some embodiments, the bacterial infection is *C. difficile*.

"Infection" as used herein refers to the invasion of one or more microorganisms such as bacteria, viruses, fungi, yeast, or parasites in the body of a patient in which they are not normally present. In certain embodiments, the infection is from a bacteria such as a *C. difficile*.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compositions, fusion proteins or polypeptides of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19*th* ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, the fusion protein, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration nasally, orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. In particular, carriers for parenteral administration include aqueous solutions of dextrose, saline, pure water, ethanol, glycerol, propylene glycol, peanut oil, sesame oil, polyoxyethylene-block polymers, and the like. Injectable solutions, for example, may be prepared in which the carrier comprises saline solution, glucose solution or a mixture of saline and glucose solution. The compositions, fusion proteins or polypeptides can also be incorporated into liposomes or administered via transdermal pumps or patches.

The compositions of the invention can further include at least one adjuvant. Adjuvants contain agents that can enhance the immune response against substances that are poorly immunogenic on their own (see, for example, Immunology Methods Manual, vol. 2, I. Lefkovits, ed., Academic Press, San Diego, Calif, 1997, ch. 13). Immunology Methods Manual is available as a four volume set, (Product Code Z37,435-0); on CD-ROM, (Product Code Z37,436-9); or both, (Product Code Z37,437-7). Adjuvants can be, for example, mixtures of natural or synthetic compounds that, when administered with compositions of the invention, such as proteins that stimulate a protective immune response made by the methods described herein, further enhance the immune response to the protein. Compositions that further include adjuvants may further increase the protective immune response stimulated by compositions of the invention by, for example, stimulating a cellular and/or a humoral response (i.e., protection from disease versus antibody production). Adjuvants can act by enhancing protein uptake and localization, extend or prolong protein release, macrophage activation, and T and B cell stimulation. Adjuvants for use in the methods and compositions described herein can be mineral salts, oil emulsions, mycobacterial products, saponins, synthetic products and cytokines. Adjuvants can be physically attached (e.g., linked by recombinant technology, by peptide synthesis or chemical reaction) to a composition described herein or admixed with the compositions described herein.

Polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain polypeptides or multichain polypeptides, such as antibodies or insulin, and may be associated or linked to each other. Most commonly, disulfide linkages are found in multichain polypeptides. The term "polypeptide" may also apply to amino acid polymers in which at least one amino acid residue is an artificial chemical analogue of a corresponding naturally-occurring amino acid.

A "polypeptide variant" is a molecule that differs in its amino acid sequence relative to a native sequence or a reference sequence. Amino acid sequence variants may possess substitutions, deletions, insertions, or a combination of any two or three of the foregoing, at certain positions within the amino acid sequence, as compared to a native sequence or a reference sequence. Ordinarily, variants possess at least 50% identity to a native sequence or a reference sequence. In some embodiments, variants share at least 80% identity or at least 90% identity with a native sequence or a reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments "variant mimics" are provided. A "variant mimic" contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic. For example, phenylalanine may act as an inactivating substitution for tyrosine, or alanine may act as an inactivating substitution for serine.

"Orthologs" refers to genes in different species that evolved from a common ancestral gene by speciation. Normally, orthologs retain the same function in the course of evolution. Identification of orthologs is important for reliable prediction of gene function in newly sequenced genomes.

"Analogs" is meant to include polypeptide variants that differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure as indicated. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more (e.g., 3, 4 or 5) amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

As used herein, "percentage of sequence identity" or "percentage of homology" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" or "substantial homology" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

The expression vectors useful in the present invention are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional sequences, such as sequences encoding a protein.

The selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a Rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available.

The term "promoter," as used herein refers to a region or regions of a nucleic acid sequence that regulates transcription.

The terms "anti-FliCD serum" and "hyperimmune serum" as used herein refer to serum containing antibodies to FliC and FliD (FliCD). In some cases, the serum is taken from subjects previously administered a fusion protein as described herein. In some embodiments, this fusion protein contains the FliC and FliD of C. difficile.

Figure 4:
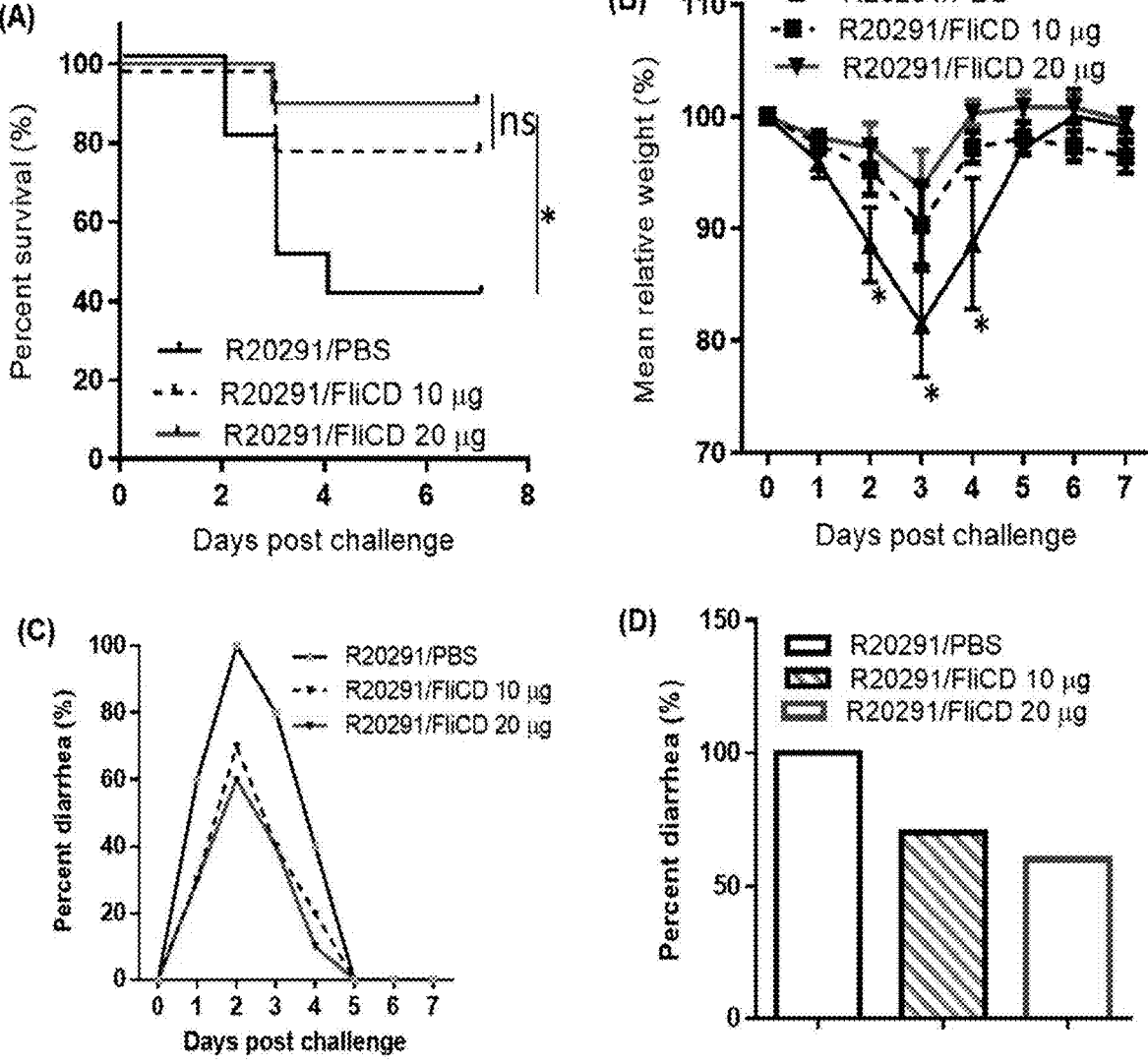
FIG. 4A-D is a series of graphs depicting immunizations of mice with FliCD provide mice significant protection against infection with *C. difficile* strain R20291. Mice were challenged with *C. difficile* R20291 spores ($10^6$/mouse) 14 days after the third immunization of groups of mice (n=10) with FliCD at 10 or 20 μg/mouse/immunization or with PBS in the presence of alum. (A) Kaplan-Meier survival plots (p=0.02 between R20291/PBS and R20291/FliCD 20 μg; p=0.0628 between the R20291/PBS and R20291/FliCD 10 μg. (B) Mean relative weight of all surviving mice (up to the day of death). Data were presented as the mean±SEM. (* p<0.05). (C, D) Frequency of diarrhea.
Figure 6:
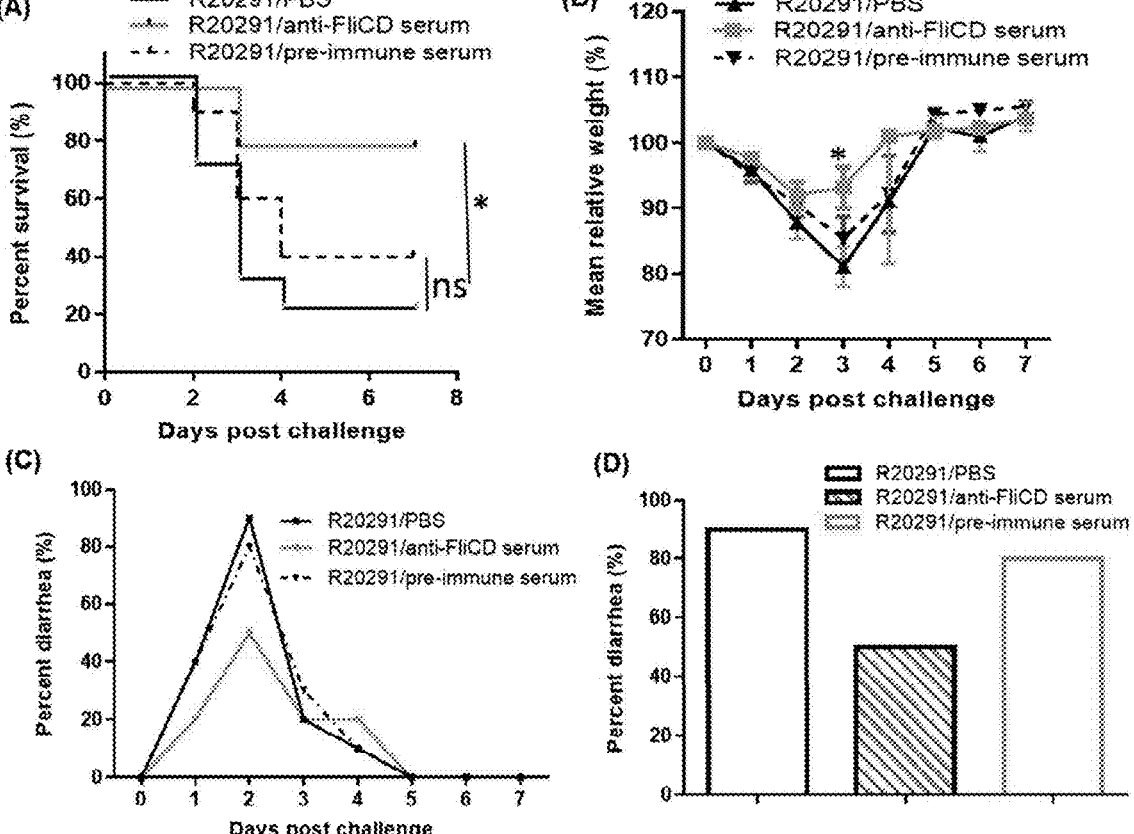
FIG. 6A-D is a series of images depicting anti-FliCD hyperimmune serum provides mice with significant protection against infection by *C. difficile* strain R20291. Three groups of mice (n=10) were i.p. administered 400 μl of anti-FliCD sera (IgG titer of $10^7$), pre-immune sera or PBS 4 h before infection with *C. difficile* R20291 ($10^7$ spores) in the mouse model of infection. (A) Kaplan-Meier survival plots (p=0.0079 between groups R20291/PBS and R20291/anti-FliCD; p=0.078 between groups R20291/PBS and R20291/pre-immune serum). (B) Mean relative weight of all surviving mice (up to the day of death) The data are presented as the mean±SEM. (C, D) Frequency of diarrhea. (*p<0.05).
Figure 8:
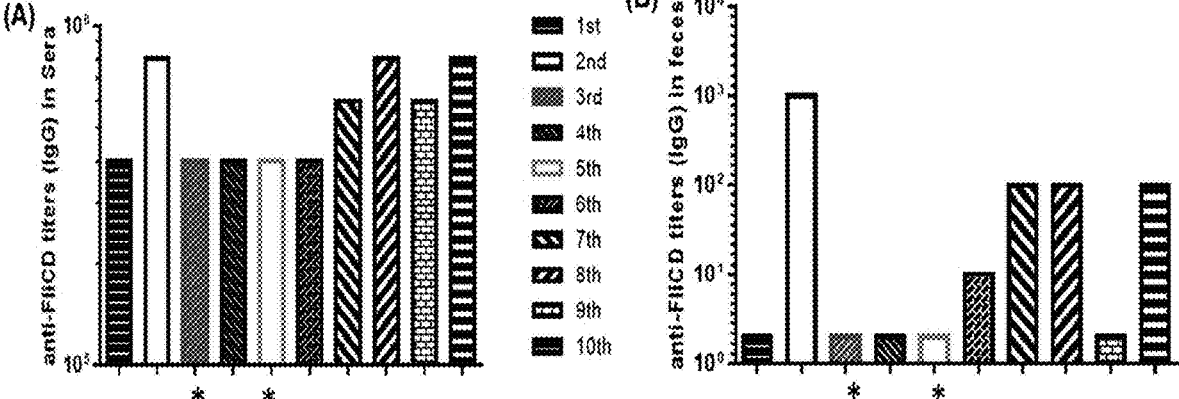
FIG. 8A-B are a series of graphs depicting anti-FliCD titers in sera and feces from mice receiving anti-FliCD hyperimmune serum and being challenged with R20291 spores. (A) Sera and (B) feces were collected on day 4 postinfection, and the anti-FliCD IgG titers were measured by standard ELISA. The data are presented as the mean±SEM (n=triplicate). (*, the sera and feces of the moribund mice were collected before the mice were euthanized.)
Figure 9:
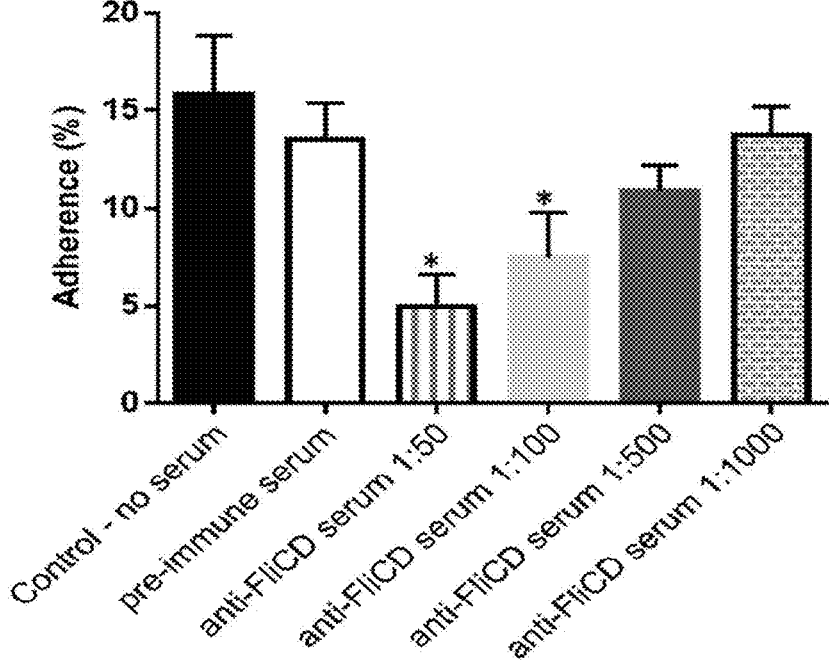
FIG. 9 is a graph depicting anti-FliCD serum inhibits the adhesion of *C. difficile* to HCT8 cells. *C. difficile* R20291 vegetative cells ($1.5\times10^6$) in 100 μl BHI were preincubated with anti-FliCD hyperimmune serum (IgG titer $10^7$) at different serum dilutions (1/50, 1/100, 1/500 and 1/1,000) or with PBS/pre-immune serum (1/50) for 30 min before being added to confluent HCT-8 cells ($1\times10^5$/well) in a 24-well plate in an anaerobic chamber. The plate was incubated at 37° C. for 100 min. After incubation, the cell-R20291 mixture was washed three times with PBS by centrifugation to collect unbound R20291 cells. The percentage of R20291 adhesion was calculated using the following formula: (initial CFU/ml–unbound CFU/ml)/initial CFU/ml. The experiments were independently repeated thrice. Data are present as the mean±SEM. (*, p<0.05, versus treatment with pre-immune serum).

Both FliC and FliD may play an important role in cell adherence, colonization, invasion and pathogenicity of C. difficile[15]. The inventors found that both FliCD immunizations and hyperimmune anti-FliCD serum protected against C. difficile infection in a mouse model (FIG. 4 and FIG. 6) and decreased C. difficile spore and toxin levels in the feces from mice that were challenged with C. difficile spores. These results indicate that anti-FliCD antibodies from active or passive immunizations may either decrease C. difficile toxin production and sporulation on a per cell basis or reduce C. difficile colonization. The further analyses support the latter scenario. In vitro, the inventors found that anti-FliCD serum inhibited the adherence of C. difficile R20291 vegetative cells to HCT8 cells (FIG. 9). This was also supported by the in vivo experiment. The inventors found that the anti-FliCD titers in the sera and feces that were collected from the C. difficile-induced moribund mice were among the mice with lower titers (FIG. 8). The inventors are conducting studies to determine whether FliCD antibodies can affect C. difficile toxin production and sporulation.

Interestingly, another study showed that both the fliC and fliD mutant strains of CD630Derm lost flagella but adhered to human intestine-derived Caco-2 cells better than did the wild-type strain, and they were also more virulent in hamsters[17], which might be partially caused by the relatively increased toxin production in the mutant strains. Their data also suggest that neither FliC nor FliD is required for the cecal colonization of hamsters. The inventors are conducting studies to further understand the phenotypic differences between a complete loss of flagella by gene silence and the direct binding of flagella proteins by antibodies.

In addition, it has been reported that C. difficile FliC can activate TLR5 in vitro[25-27], indicating that it may stimulate the TLR5 pathway in vivo and thereby provide the mice with additional protection by directly or indirectly affecting C. difficile colonization and toxin production, as has been demonstrated by another study, which showed that the activation of TLR5 pathway by Salmonella enterica serovar Typhimurium flagellin is critical in protecting mice against CDI[28]. Finally, the inventors found that flagella production is phase variable in C. difficile[29]. Antibodies generated against flagellar components presumably may not affect this flagella-off subpopulation.

The inventors constructed a fusion protein vaccine, namely, FliCD, and showed its potent efficacy as a new vaccine candidate in the mouse model of CDI. The data showed that not only did FliCD fusion protein represent an effective vaccine candidate but also anti-FliCD serum may represent an alternative therapy against CDI.

Results

Homology of FliC and FliD in Major Toxinotypes and Ribotypes of C. difficile Strains Bacterial flagellin is highly variable across species. An optional vaccine candidate should be conserved. The inventors investigated the homology of FliC and FliD proteins in major toxinotypes, including A2B1CDT1, A1B1CDT2, A2B1CDT2, and A2B2CDT2, as well as major ribotypes, including the RT027, RT078, RT017, RT012, RT003, and RT009 C. difficile strains (Table 1). Maximum likelihood phylogenetic trees were generated using the FliC (FIG. 1A) and FliD (FIG. 1B) amino acid sequences. Both the RT027 FliC and FliD sequences cluster together, as do the RT017 FliC and FliD sequences. There are no sequence variations within either ribotype group. This is in line with a previous study that observed no sequence differences between FliC and FliD sequences in RT027 and RT176 isolates (19). There does not appear to be a strong correlation between toxinotype and either FliC or FliD sequence relatedness among the strains that were selected.

TABLE 1

*C. difficile* strains used for the homology analysis of FliC and FliD

| Toxinotype | Strain | Ribotype | Database | Accession no./barcode | Reference |
|---|---|---|---|---|---|
| A⁻B⁻CDT⁻ | R20291 | RT027 | GenBank | FN545816.1 | 30 |
| | CD196 | RT027 | GenBank | FN538970.1 | 31 |
| | M120 | RT078 | GenBank | FN665653.1 | 32 |
| A⁻B⁻CDT⁻ | VPI 10463 | RT003 | Enterobase | CLO__AA6882AA | 33 |
| | CD630 | RT012 | GenBank | AM180355.1 | 34 |
| A⁻B⁻CDT⁻ | M68 | RT017 | GenBank | NC_017175.1 | 35 |
| | DSM 29627 | RT017 | GenBank | CP016102.1 | 36 |
| | Xy06 | RT017 | GenBank | NZ__JANFNF000000000.1 | GenBank |
| | 1470 | RT017 | GenBank | NZ__OEZL00000000.1 | 38 |
| | 8864 | RT59 | GenBank | NZ__OFZE00000000.1 | 39 |
| | SUC36 | RT078 | GenBank | NZ__OEZZ00000000.1 | 40 |
| | ES130 | SLO101 | GenBank | NZ__OFZV00000000.1 | 40 |
| | WA151 | SKO098 | GenBank | NZ__OEZY00000000.1 | 40 |
| | 173070 | RT015 | GenBank | NZ__OEZH00000000.1 | 40 |
| A⁻B⁻CDT⁻ | CD37 | RT09 | GenBank | NZ__AHJJ00000000.1 | 41 |
| | CCUG37785 | ND | GenBank | NZ__JAGKRT000000000.1 | 42 |

To better illustrate the sequence diversity, FliC and FliD sequences were aligned using MUSCLE and visualized in Jalview software. Most sequence variations in FliC were observed between the amino acid positions 108 and 245 (using R20291 FliC as a reference), which is in concordance with the results of a previous study that reported the N terminus and C terminus of FliC to be more conserved than the center region 2. Three strains, namely, R20291, CD196, and 173070, encode FliC proteins with an additional 29 amino acid residues on their N termini. These residues were absent in all of the other strains that were examined. The R20291 and CD196 sequences are identical on account of both strains being ribotype RT027, but these sequences are also quite similar to the 173070 N terminus sequence (86% identical), despite strain 173070 being classified as a single-ton in the phylogenetic tree (FIG. 1A).

In FliD, a flagellar cap protein[21], sequence variations are distributed more widely throughout the sequence. Flagellar caps assume a structural role by preventing the loss of flagellin monomers while also facilitating the excretion of various proteins[22,23]. The exposure of FliD to the external environment, such as to immune cells, may provide selective pressure for mutations throughout the protein that facilitate immune evasion. In strain VPI 10463, the fliD gene was unique among the strains examined, which accounts for the observation that the amino acid residues 286 to 295 of VPI 10463 FliD do not align with any of the other sequences that were examined. Upon viewing the annotated genome of VPI 10463, the fliD gene was found to be split roughly in half between two adjacent open-reading frames (ORFs). These two ORFs are not on the same reading frame, but they do overlap at the highlighted regions. The fragmentation of the VPI 10463 fliD gene could potentially compromise the flagellin structure of this strain. Overall, FliC and FliD are rather conserved among the selected *C. difficile* strains, which is also in concordance with the results of previous studies.[16,20]

Immunization of Mice with FliCD Induces Significant Anti-FliCD Responses in Mice Gene sequences encoding full-length FliC and FliD from *C. difficile* R20291 were bridged with a linker (ggt ggc tct ggt) (SEQ ID NO: 1), synthesized, and cloned into pHis1525 in *Bacillus megaterium*

Figure 2:
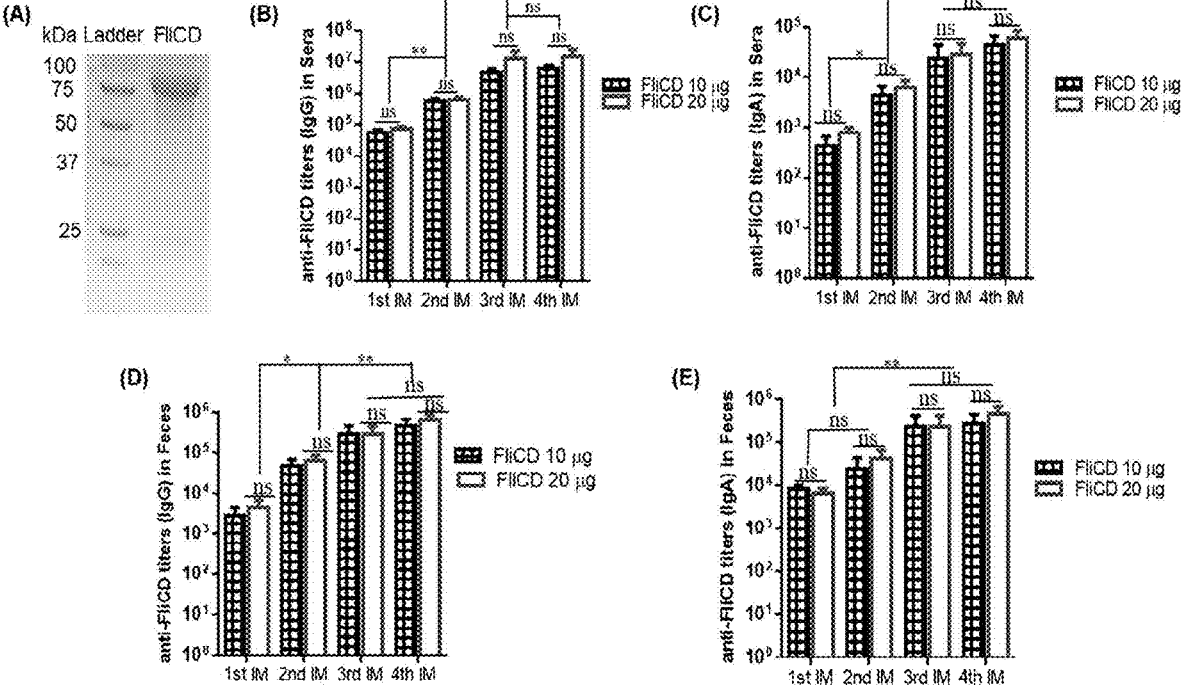
FIG. 2A-E are a series of images depicting expression and purification of protein FliCD. (A) The gene sequence encoding FliCD was synthesized and cloned in *Bacillus megatarium*. FliCD was purified from bacterial lysate by Ni-affinity chromatography and analyzed by SDS-PAGE. (B-E) FliCD immunizations via intraperitoneal (i.p.) route induce anti-FliCD antibody responses. Groups of C57 BL/6 mice (n=10) were immunized 4 times at 12-day intervals with 10 or 20 μg of FliCD with alum as an adjuvant. Sera and feces were collected, and anti-FliCD IgG/IgA titers were measured via standard ELISA. Data are presented as mean±SEM (*p<0.05; **p<0.01; ns, not significant).
Figure 3:
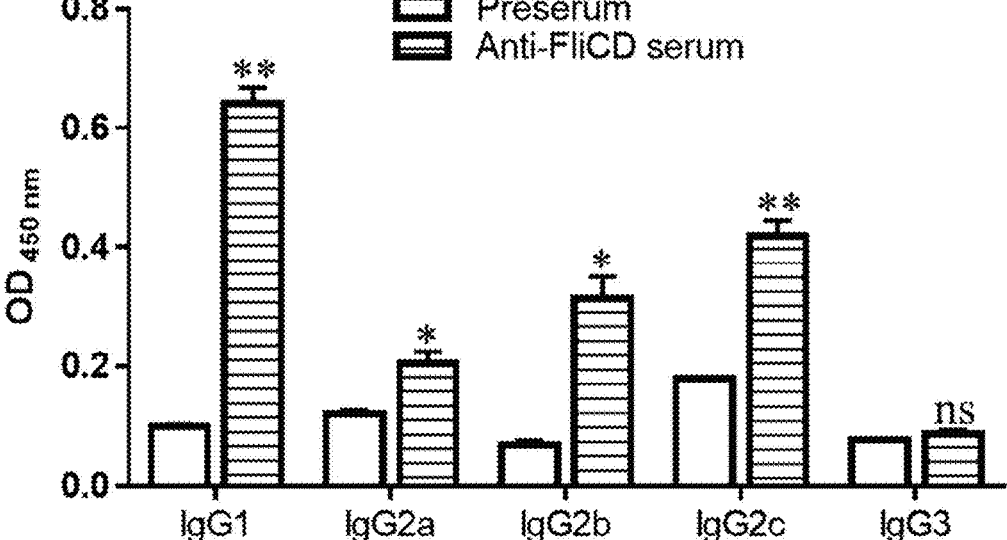
FIG. 3 is a graph depicting anti-FliCD IgG isotypes of sera from mice immunized with FliCD. Mice were immunized with FliCD three times, and serum samples were collected. The anti-FliCD IgG isotypes of the pooled serum samples from the third immunization were measured via standard ELISA. Data are presented as the mean±SEM (n=triplicate) (*p<0.05; **p<0.01; ns, not significant).

Recombinant FliCD with a 6×His tag (97 kDa) was purified via Ni-NTA affinity chromatography to a purity >95% (FIG. 2A). The immunizations of mice with 10 or 20 µg FliCD with alum as an adjuvant via the intraperitoneal (i.p.) route induced high levels of IgG and IgA antibody responses against FliCD in sera (FIGS. 2B and C) and in feces (FIGS. 2D and E). However, no significant increases of anti-FliCD antibodies were observed between the third and fourth immunizations. Also, the titers were not signifi-cantly higher in the sera or feces of mice immunized with 20 µg FliCD, compared to 10 µg FliCD, after the third and fourth immunizations. To determine the natures of the anti-FliCD immune responses, the inventors determined an anti-FliCD IgG isotype (FIG. 3). Immunizations with FliCD induced significantly high levels of IgG1, IgG2C, IgG2b, and IgG2a anti-FliCD isotypes, indicating balanced Th2 (IgG1) and Th1 (IgG2a, IgG2b, IgG2C) immune responses.

Figure 5:
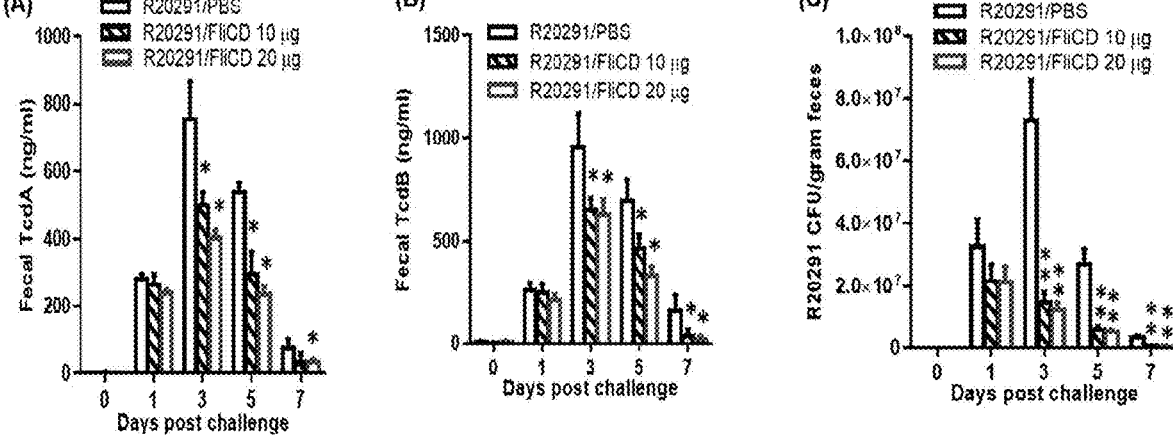
FIG. 5A-C are a series of graphs depicting immunizations of mice with FliCD decrease the *C. difficile* spores and toxins in feces after a challenge with *C. difficile* spores. TcdA (A) or TcdB (B) levels in feces were determined via ELISA. (C) R20291 spore concentrations in feces. Data are presented as the mean±SEM (n=10) (*p<0.05, **p<0.01 versus PBS).

Immunization with FliCD Protects Mice Against *C. difficile* Infection and Decreases the Spore and Toxin Levels in their Feces The protection efficacy of FliCD immunization was fur-ther evaluated in a mouse model of CDI. 3 groups of mice (n=10) were immunized thrice via the i.p. route with 10 µg/20 µg of FliCD or PBS with alum at 12-day intervals. After the third immunization, the mice were challenged with $10^6$ spores of *C. difficile* R20291, which is a hypervirulent strain of ribotype 027. The control (PBS-immunized) mice exhibited significant disease symptoms, including weight loss (FIG. 4B) and severe diarrhea (FIGS. 2C and D). Approximately 60% of the mice succumbed by day 4 (FIG. 4A). In contrast, the FliCD-immunized mice developed much less severe disease symptoms, including less weight loss (FIG. 3B) and lower diarrhea rates (FIGS. 4C and D) as well as a significantly higher survival rate (80% for the 10 µg FliCD-immunized mice and 90% for the 20 µg FliCD-immunized mice) (FIG. 4A). The FliCD-immunized mice excreted significantly smaller amounts of TcdA (FIG. 5A) and TcdB (FIG. 5B) in their feces, compared to the PBS group. The fecal samples of the FliCD-immunized mice contained significantly fewer R20291 spores, compared to the control group (FIG. 5C).

Anti-FliCD Serum Protects Mice Against *C. difficile* Infec-tion and Decreases the Spore and Toxin Levels in their Feces To elucidate how FliCD-immunized mice gain resistance to CDI, the inventors tested whether the hyperimmune serum (anti-FliCD serum) provides protection against infec-tion. Anti-FliCD serum (IgG titer of $10^7$) was collected from mice that were immunized 4 times with 10 µg FliCD. 3 groups of mice (n=10) were i.p. administered 400 µL of anti-FliCD serum, pre-immune serum, or PBS 4 h before infection with *C. difficile* R20291 spores ($10^6$) in the mouse model of infection. The majority of the PBS and pre-immune serum groups developed diarrhea (90% in the PBS group and 80% in the pre-immune serum group) (FIGS. 6C and D) and significant weight loss (FIG. 6B), with survival rates of 20% and 40% being observed in the PBS group and the pre-immune serum group, respectively (FIG. 67A), whereas the mice that were administered 400 μL of hyper-immune serum developed much less severe disease symptoms, including less weight loss (FIG. 6B) and a lower diarrhea rate (50%) (FIG. 7C) as well as a significantly higher survival rate (80%) (FIG. 67A).

Figure 7:
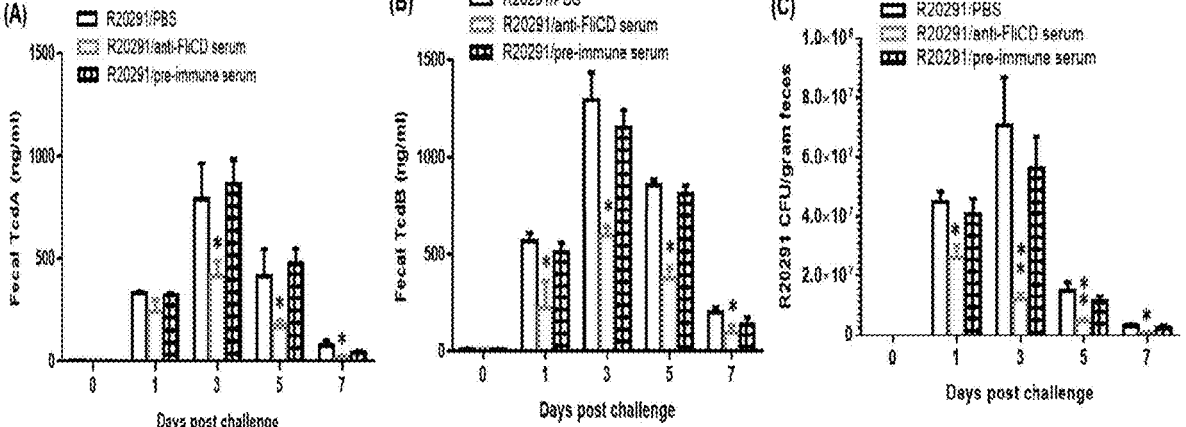
FIG. 7A-C are a series of graphs depicting anti-FliCD titers in sera and feces from mice administered with anti-FliCD hyperimmune serum and challenged with R20291 spores. (A) Sera and (B) feces were collected at day 4 postinfection, and the anti-FliCD IgG titers were measured via standard ELISA. The data are presented as the mean±SEM (n=triplicate). (*, the sera and feces of the moribund mice were collected before the mice were euthanized.)

The mice that were administered the anti-FliCD serum excreted significantly smaller amounts of TcdA (FIG. 7A) and TcdB (FIG. 7B) in the feces that were collected on days 1 to 7 postinfection, compared to those of the PBS and the pre-immune sera groups. The fecal samples that were collected from the mice that were administered the anti-FliCD serum contained significantly fewer R20291 spores, compared to the PBS and the pre-immune serum groups (FIG. 7C). High levels of anti-FliCD antibodies were also detected in the sera and the feces that were collected from the mice that were administered the anti-FliCD serum (FIG. 8). The third and fifth mice in this group, whose weight loss values were 20%, were among those with the lowest anti-FliCD titers in the sera and feces, affirming the protection of the anti-FliCD antibodies against CDI in the mice.

Anti-FliCD Serum Inhibits the Binding of *C. difficile* to HCT8 Cells

When the anti-FliCD serum was diluted 1 to 50 or 1 to 100 in the cells medium, the adherence rate of the *C. difficile* R20291 vegetative cells to HCT8 cells significantly decreased compared with that of HCT8 cells treated with preserum (5.0±0.7% or 7.5±0.9% versus 13.6±0.7%). When the serum was diluted 1 to 500, the adherence rate decreased to 10.9±0.6%, but this decrease was not statistically significant (FIG. 9).

Materials and Methods

Homology Analysis of FliC and FliD.

*C. difficile* strains (Table 1) were chosen for analysis based on the results of previous studies[30-42]. The genomes of each strain were accessed through GenBank (National Center for Biotechnology Information) or the Enterobase *Clostridioides* database[43]. The amino acid sequences for FliC and FliD were mined from each genome before the performance of MUSCLE alignments in MegaX software[44] using the default parameters. Maximum likelihood phylogenetic trees were constructed in MegaX with 500 bootstrap replicates. The cluster patterns of the phylo-genetic trees were used to order the sequences of FliC or FliD for a second MUSCLE alignment on the MPI Bioinformatics Toolkit server[45,46], as this application produces an output file that is suitable for visualization using Jalview[47]. Jalview calculates conservation scores for MUSCLE alignments according to a previously defined algorithm[48] that assesses both the amino acid identity as well as the physico-chemical properties of the amino acids at a given position to produce a score between 0 (no similarities) and 11 (identical amino acids).

Animals

Animal studies followed the Guide for the Care and Use of Laboratory Animals of the National Institutes of Health and were approved by the Institute Animal Care and Use Committee (IACUC) at the University of South Florida. Wild-type C57BL/6 mice were purchased from Charles River Laboratories.

Expression and Purification of Recombinant Fusion Protein FliCD

Gene sequences encoding FliC and FliD from *C. difficile* R20291[49] (Accession No. NZ_CP029423.1) were bridged with a linker sequence (ggt ggc tct ggt) (SEQ ID NO: 1), which encodes aa sequence GGSG (SEQ ID NO: 2), synthesized by Geneart (Germany) and cloned between BsrGI and EagI restriction sites of pHis1525[24]. FliCD was expressed in *B. megaterium* and purified as described previously[50].

FliC aa sequence (Locus tag: CDIF27147_00364) -

(SEQ ID NO: 3)

MSDYINEELIKKIKSRNDKDVNYTKEGKIMRVNTNVSALIANNQMGRNVN

AQSKSMEKLSSGVRIKRAADDAAGLAISEKMRAQIKGLDQAGRNVQDGIS

VVQTAEGALEETGNILQRMRTLSVQSSNETNTAEERQKIADELLQLKDEV

ERISSSIEFNGKKLLDGSSTEIRLQVGANFGTNVAGTTNNNNEIKVALVN

TSSIMSKAGITSSTIASLNADGTSGTDAAKQMVSSLDVALKELNTSRAKL

GAQQNRLESTQNNLNNTIENVTAAESRIRDTDVASEMVNLSKMNILVQAS

QSMLAQANQQPQGVLQLLG encoded by (SEQ ID NO: 4)

atgtccgattatataaatgaagaattaataaaaaagattaaaagtagaaa tgacaaggatgtcaactatactaaggagggtaaaataatgagagttaata caaatgtaagtgctttgatagcaaataaccaaatgggaagaaacgtaaat gcacaaagtaagtctatggagaagttatcttctggtgttagaattaagag agctgctgatgatgctgctgggcttgctatatctgagaaaatgagagctc aaataaaaggtttagaccaagcaggaagaaacgttcaagatggtatatct gttgcacaaacagcagaaggtgcattagaagaaactggtaatatactaca aagaatgagaactttatcagtacaatcttcaaatgaaactaatactgctg aagaaagacaaaagatagctgatgagttgttacaattaaaggatgaagtt gaaagaatatcaagctcaattgagtttaatggtaagaaattacttgatgg aagttctacagaaataagattacaagttggagctaattttggaacaaatg ttgcaggaacaactaacaacaacaatgaaataaaagttgctctagtaaat acttcaagtataatgagtaaagcaggtataacaagttctacaatagcaag cttaaatgcagatggaacttctggaacagatgcagctaaacaaatggtgt ctagcttagatgtagctcttaaagaattaaatacatcaagagcaaaatta ggggcacaacaaaatagactagaatcaactcaaaacaacttaaataatac tatagaaaatgttacagcagctgaatcaagaataagagatacagatgttg cttcagaaatggttaacttatctaaaatgaatatattagttcaagcatca cagtcaatgcttgctcaagctaatcagcaaccacaaggagttttacaatt attaggataa -continued FliD aa sequence (Locus tag:
CDIF27147_00362) -
(SEQ ID NO: 5)
MSSISPIRVTGLSGNFDMEGIIEASMIRDKEKVDKAKQEQQIVKWKQEIY

RNVIQESKDLYDKYLSVNSPNSIVSEKAYSSTRITSSDESIIVAKGSAGA

EKINYQFAVSQMAEPAKFTIKLNSSEPIVRQFPPNASGASSLTIGDVNIP

ISEQDTTSTIVSKINSLCADNDIKASYSEMTGELIISRKQTGSSSDINLK

VIGNDNLAQQIANDNGITFANDASGNKVASVYGKNLEADVTDEHGRVTHI

SKEQNSFNIDNIDYNVNSKGTAKLTSVTDTEEAVKNMQAFVDDYNKLMDK

VYGLVTTKKPKDYPPLTDAQKEDMTTEEIEKWEKKAKEGILRNDDELRGF

VEDIQSAFFGDGKNIIALRKLGINESENYNKKGQISFNADTFSKALIDDS

DKVYKTLAGYSSNYDDKGMFEKLKDIVYEYSGSSTSKLPKKAGIEKTASA

SENVYSKQIAEQERNISRLVEKMNDKEKRLYAKYSALESLLNQYSSQMNY

FSQAQGN encoded by (SEQ ID NO: 6)
ATGTCAAGTATAAGTCCTATAAGAGTTACAGGTCTTTCAGGAAATTTTGA

TATGGAAGGCATAATCGAAGCTAGTATGATTAGAGACAAGGAAAAAGTTG

ATAAAGCAAAACAAGAACAACAAATCGTTAAATGGAAGCAAGAAATATAT

AGAAATGTTATACAAGAATCAAAAGATCTTTATGATAAATATCTAAGCGT

AAATTCTCCTAATAGTATAGTAAGTGAAAAAGCATACTCTTCTACAAGAA

TAACCAGTTCTGATGAAAGTATTATAGTAGCAAAAGGCTCAGCTGGTGCA

GAAAAAATAAATTATCAATTTGCAGTTTCTCAAATGGCTGAACCAGCAAA

ATTTACTATTAAATTAAATTCAAGTGAACCTATTGTTCGACAGTTCCCTC

CAAATGCCAGTGGAGCTAGTTCTTTAACTATAGGAGATGTAAATATACCA

ATATCTGAACAAGATACTACAAGTACTATTGTAAGTAAGATAAACTCCCT

TTGCGCAGATAATGATATAAAGGCTTCTTATAGTGAGATGACAGGTGAAT

TGATTATTTCGAGAAACAAACTGGTTCGTCATCAGACATTAATTTAAAA

GTAATTGGAAATGACAATTTAGCTCAGCAAATTGCTAATGATAATGGTAT

CACATTTGCAAATGATGCTAGTGGAAACAAAGTGGCAAGTGTATATGGAA

AAAATCTAGAAGCTGATGTAACTGATGAACATGGAAGAGTAACTCATATA

AGTAAAGAACAAAATTCATTTAATATAGATAATATTGACTATAATGTAAA

TTCAAAAGGAACTGCAAAGTTGACTTCTGTCACTGATACTGAAGAAGCTG

TTAAAAATATGCAAGCATTTGTGGATGATTATAATAAACTGATGGACAAG

GTCTATGGTTTAGTTACTACTAAAAAACCAAAAGATTATCCGCCTCTTAC

AGATGCCCAAAAAGAAGATATGACAACTGAAGAAATAGAAAAATGGGAAA

AGAAAGCTAAAGAAGGTATACTTAGAAATGATGATGAGTTAAGAGGTTTT

GTTGAAGATATTCAGTCTGCATTTTTTGGAGATGGAAAAAATATTATTGC

ATTAAGAAAACTAGGTATCAATGAAAGCGAAAATTACAATAAAAAAGGTC

AAATATCATTTAATGCAGATACTTTTTCAAAGGCTCTTATAGATGATAGT

GATAAGGTATACAAAACACTAGCAGGTTATTCTTCGAATTATGATGATAA

GGGAATGTTTGAAAAGCTAAAAGATATTGTATATGAATATTCTGGAAGTT

-continued
CAACTTCTAAACTTCCTAAAAAAGCAGGTATAGAAAAAACTGCTTCTGCT

AGTGAAAATGTATATTCAAAACAAATTGCAGAGCAAGAAAGAAATATAAG

CAGGTTAGTTGAAAAAATGAATGATAAAGAGAAAAGACTTTATGCTAAAT

ATTCAGCCTTAGAATCTTTGTTGAATCAGTATTCTTCCCAAATGAATTAT

TTCTCACAAGCACAGGGTAATTAA

An exemplary fusion protein as disclosed herein contains the following sequence (linker underlined):

(SEQ ID NO: 7)
MSDYINEELIKKIKSRNDKDVNYTKEGKIMRVNTNVSALIANNQMGRNV

NAQSKSMEKLSSGVRIKRAADDAAGLAISEKMRAQIKGLDQAGRNVQDG

ISVVQTAEGALEETGNILQRMRTLSVQSSNETNTAEERQKIADELLQLK

DEVERISSSIEFNGKKLLDGSSTEIRLQVGANFGTNVAGTTNNNNEIKV

ALVNTSSIMSKAGITSSTIASLNADGTSGTDAAKQMVSSLDVALKELNT

SRAKLGAQQNRLESTQNNLNNTIENVTAAESRIRDTDVASEMVNLSKMN

ILVQASQSMLAQANQQPQGVLQLLGGGSGMSSISPIRVTGLSGNFDMEG

IIEASMIRDKEKVDKAKQEQQIVKWKQEIYRNVIQESKDLYDKYLSVNS

PNSIVSEKAYSSTRITSSDESIIVAKGSAGAEKINYQFAVSQMAEPAKF

TIKLNSSEPIVRQFPPNASGASSLTIGDVNIPISEQDTTSTIVSKINSL

CADNDIKASYSEMTGELIISRKQTGSSSDINLKVIGNDNLAQQIANDNG

ITFANDASGNKVASVYGKNLEADVTDEHGRVTHISKEQNSFNIDNIDYN

VNSKGTAKLTSVTDTEEAVKNMQAFVDDYNKLMDKVYGLVTTKKPKDYP

PLTDAQKEDMTTEEIEKWEKKAKEGILRNDDELRGFVEDIQSAFFGDGK

NIIALRKLGINESENYNKKGQISFNADTFSKALIDDSDKVYKTLAGYSS

NYDDKGMFEKLKDIVYEYSGSSTSKLPKKAGIEKTASASENVYSKQIAE

QERNISRLVEKMNDKEKRLYAKYSALESLLNQYSSQMNYFSQAQGN

Preparation of *C. difficile* Spores

Sporulation of *C. difficile* R20291 strains was induced in Clospore medium as described previously[51]. Briefly, an overnight 20 ml *C. difficile* culture in Columbia Broth was inoculated into 500 ml of Clospore medium and incubated for 1 to 2 weeks at 37° C. in an anaerobic incubator. The spore suspension was centrifuged at 10,000×g for 20 min, and the pellet was washed 5 times with sterile water and suspended in 10 ml of ddH₂O. The spore suspension was layered onto the top of 10 ml of 50% (wt/vol) sucrose in water in a 15 ml tube. The gradient was centrifuged at 3200×g for 20 min, after which the spore pellet at the bottom was washed five times with ddH₂O to remove the sucrose and was resuspended in sterile ddH₂O. The spore preparations were >99% pure[52] and the spore concentration was determined by serial dilution on TCCA or BHI plates.

Immunization and Mouse Model of CDI

Female C57/BL6 mice were housed under the same conditions at a semi-natural light cycle of 14 h:10 h (light: dark) in a specific pathogen-free (SPF) environment. 3 groups of mice (n=10) were immunized via the i.p. route with 10 μg or 20 μg FliCD or PBS with alum as an adjuvant 3 times at 12-day intervals. Sera were collected, and anti-FliCD IgG titers were determined via ELISA. 7 days after the final immunization, the mice were given drinking water containing a mixture of 5 antibiotics, including kanamycin (40 mg/kg), gentamicin (3.5 mg/kg), colistin (4.2 mg/kg), metronidazole (21.5 mg/kg), and vancomycin (4.5 mg/kg) for 4 days, and they then received autoclaved water for 2 days, and this was followed by the i.p injection of a dose of clindamycin (10 mg/kg) before a challenge with $10^6$ *C. difficile* R20291 spores/mouse via oral gavage as described previously[53]. After infection, the mice were monitored daily for a week for survival, weight changes, diarrhea, and other symptoms of the disease. Diarrhea was defined as wet tails and loose or watery feces. The death count included the number of mice that died after infection and the number of mice that were euthanized when their weight loss was >20%.
Evaluation of Anti-FliCD Sera in the Protection of Mice Against CDI Mice (n=10) were immunized 4 times at 12-day intervals via the i.p. route with 10 µg of FliCD in PBS with alum as an adjuvant. 14 days after the fourth immunization, serum was collected and defined as hyperimmune anti-FliC serum (IgG titer of $10^7$). The mouse model of *C. difficile* infection was established as described above, except that the mice were challenged with $10^7$ *C. difficile* R20291 spores. 4 hours prior to infection with spores, 400 µl of hyperimmune serum, pre-immune serum, or PBS were administered (i.p.) to each mouse in 3 groups, respectively.
ELISA for Anti-FliCD IgG ELISA was performed as previously described[50]. Briefly, Costar 96-well ELISA plates were coated with 100 µL/well of FliCD (0.5 µg/ml) at 4° C. overnight. Following washing of the unbound material, plates were blocked with 300 µL of blocking buffer (PBS+5% dry milk) at room temperature for 2 h. After washing, 100 µL of 10-fold diluted sera or fecal samples were added into each well of the plates and were incubated for 1.5 hours at room temperature. Following washing with PBS, 100 µL of mouse IgG-HRP (1:3000) were added to each well and incubated for 30 min to 1 h. After the washing step with PBS, substrate TMB was added to allow for color development at room temperature for 5 to 30 min. The reaction was stopped via the addition of $H_2SO_4$ to each well, and the OD values at 450 nm were recorded using a spectrophotometer. The anti-toxin and anti-FliCD IgG titer of a given sample (a serum or fecal sample from immunized mouse) is defined as the dilution factor at which the $OD_{450\ nm}$ is greater or equal to twice that of the serum or fecal samples that were collected from mice before immunization.
Quantification of *C. difficile* Spores in Mouse Feces Fecal samples were collected on days 0, 1, 3, 5 and 7 post infection. 50 mg of feces were dissolved in 500 µl sterile water for 16 h at 4° C., and they were then treated with 500 µl of absolute ethanol (Sigma-Aldrich) for 1 h at room temperature to kill vegetative cells. The samples were vortexed, serially diluted and plated onto selective medium supplemented with taurocholate (0.1% w/v), Cefoxitin (8 µg/mL), and D-cycloserine (250 µg/mL). The plates were incubated anaerobically at 37° C. for 48 h. The colonies were counted, and data were expressed as CFU/gram of feces.
Quantitation of *C. difficile* Toxins in Mouse Feces After a challenge with *C. difficile* spores, feces were collected and dissolved in PBS (0.1 g/ml) containing a protease inhibitor cocktail. Supernatants were collected after centrifugation and were used for the determination of TcdA/TcdB concentrations via ELISA. Briefly, 96-well Costar microplates were coated with 100 µl of the anti-TcdA antibody (1 µg/ml) and the anti-TcdB antibody (1 µg/ml) overnight in phosphate-buffered saline (PBS) at 4° C. The next day, each well was blocked with 300 µl of blocking buffer (PBS+5% dry milk) at RT for 2 h. Next, standards and samples were added to each well (100 µl) in duplicate, and incubated for 90 min at 25° C. After another set of washings, HRP-chicken anti-*C. difficile* TcdA/TcdB (1:5,000 dilution in PBS, *Gallus* Immunotech, Shirley, MA) was added to wells for 30 min at RT. A final set of 3-washing preceded the addition of the TMB microwell peroxidase substrate for 20 min at RT in the dark. The reaction was stopped with 2 M of $H_2SO_4$, and the absorbance was measured using a plate reader at 450 nm.
Adhesion Inhibition Assays The adherence of *C. difficile* R20291 vegetative cells to human gut epithelial cells was assessed as described previously[54]. Briefly, HCT-8 cells were grown to 95% confluence ($1\times10^5$/well) in a 24-well plate and were then moved into an anaerobic chamber. This was followed by infection with $1.5\times10^6$ log phase R20291 vegetative cells at a multiplicity of infection (MOI) of 15:1. The plate was incubated at 37° C. for 100 min in an anaerobic chamber. R20291 vegetative cells in 100 µl of BHI medium were preincubated with hyperimmune serum (IgG titer of $10^7$) at different serum dilutions (1/50, 1/100, 1/500 and 1/1000) for 30 min before being added to the cells. After incubation, the cell-*C. difficile* mixture was washed three times with 1×PBS via centrifugation at 800×g for 1 min to remove any unbound R20291. The supernatants were collected after the centrifugation of each wash step to enumerate any R20291 that did not adhere to the cells. The R20291 colonies in the supernatant were enumerated on pre-reduced BHI agar. As a control, the R20291 strain was incubated with either PBS or pre-immune sera (1/50), and adhesion assays were performed in triplicate. The percentage of R20291 adhesion was estimated using the following formula: (initial CFU/ml–eluted CFU/ml)/initial CFU/ml.
Statistical Analysis Survival curves were analyzed by Kaplan-Meier with a log-rank test of significance analysis. The data for comparisons between two groups were analyzed by Student's unpaired t-tests for statistical significance. The data for comparisons between more than two groups were analyzed by one-way analysis of variance (ANOVA) with post-hoc analysis via Bonferroni tests. The data are expressed as the mean±the standard error of the mean (SEM). Differences were considered statistically significant if P<0.05 (*). All statistical analyses were performed using GraphPad Prism software.

The following non-limiting examples illustrate exemplary systems and components thereof in accordance with various embodiments of the disclosure. The examples are merely illustrative and are not intended to limit the disclosure in any way.

Example 1—Method of Preventing *C. difficile* Infection (Prophetic)

A 35 year old female patient is administered a therapeutically effective amount of a vaccine comprised of a fusion protein having SEQ ID NO: 7 and a pharmaceutically acceptable carrier intranasally. The patient is exposed to *C. difficile* and does not contract CDI.

A 45 year old female patient is administered a therapeutically effective amount of anti-FliCD serum intranasally. The patient is exposed to *C. difficile* and does not contract CDI.

A 39 year old male patient is administered a therapeutically effective amount of a vaccine comprised of a fusion protein having SEQ ID NO: 7 and a pharmaceutically acceptable carrier via parenteral injection. The patient is exposed to *C. difficile* and does not contract CDI.

A 55 year old male patient is administered a therapeutically effective amount of anti-FliCD serum via parenteral injection. The patient is exposed to *C. difficile* and does not contract CDI.

Example 2—Method of Treating *C. difficile* Infection (Prophetic)

A 49 year old male patient presents with severe diarrhea and weight loss. A diagnosis of CDI is confirmed. The patient is administered a therapeutically effective amount of a therapeutic agent comprised of anti-FliCD serum via parenteral injection. After a period of time, the patient's symptoms resolve. The patient is subsequently tested and *C. difficile* is not found.

A 35 year old female patient presents with diarrhea and weight loss. A diagnosis of CDI is confirmed. The patient is administered a therapeutically effective amount of a therapeutic agent comprised of a fusion protein having SEQ ID NO: 7 and a pharmaceutically acceptable carrier via parenteral injection. After a period of time, the patient's symptoms resolve. The patient is subsequently tested and *C. difficile* is not found.

A 59 year old female patient presents with severe diarrhea and weight loss. A diagnosis of CDI is confirmed. The patient is rectally administered a therapeutically effective amount of a therapeutic agent comprised of anti-FliCD serum. After a period of time, the patient's symptoms resolve. The patient is subsequently tested and *C. difficile* is not found.

A 30 year old male patient presents with diarrhea and weight loss. A diagnosis of CDI is confirmed. The patient is rectally administered a therapeutically effective amount of a therapeutic agent comprised of a fusion protein having SEQ ID NO: 7 and a pharmaceutically acceptable carrier. After a period of time, the patient's symptoms resolve. The patient is subsequently tested and *C. difficile* is not found.

CONCLUSION

The inventors constructed a fusion protein vaccine FliCD (containing FliC and FliD) which exhibited potent efficacy as a new vaccine candidate in experimental mouse models of CDI. The data showed that, not only does the FliCD fusion protein represent an effective vaccine candidate, but also anti-FliCD serum may represent an alternative therapy against CDI.

The sequence listing entitled "Recombinant Fusion Protein Vaccine Containing *Clostridioides* FliC and FliD" in XML format, created on Dec. 19, 2023 and being 12,000 bytes in size, is hereby incorporated by reference into this disclosure.

REFERENCES

1. Curry, S. R., *Clostridium difficile*. Clinics in Laboratory Medicine, 2017. 37(2): p. 341-69.
2. Moreno, M. A., F. Furtner, and F. P. Rivara, *Clostridium difficile: A Cause of Diarrhea in Children*. Jama Pediatrics, 2013. 167(6): p. 592-592.
3. Kuehne, S. A., et al., *The role of toxin A and toxin B in Clostridium difficile infection*. Nature, 2010. 467(7316): p. 711-713.
4. Guh, A. Y. and P. K. Kutty, *Clostridioides difficile Infection*. Ann Intern Med, 2018. 169(7): p. ITC49-354 ITC64.
5. Bouwknegt, M., S. van Dorp, and E. Kuijper, *Burden of Clostridium difficile Infection in the United States*. New England Journal of Medicine, 2015. 372(24): p. 2368-2368.
6. Lessa, F. C., C. V. Gould, and L. C. McDonald, *Current Status of Clostridium difficile Infection Epidemiology*. Clinical Infectious Diseases, 2012. 55: p. S65-S70.
7. Marra, A. R., et al., *Incidence and Outcomes Associated With Clostridium difficile Infections: A Systematic Review and Meta-analysis*. Jama Network Open, 2020. 3(1).
8. Drekonja, D. M., et al., *Comparative Effectiveness of Clostridium difficile Treatments A Systematic Review*. Annals of Internal Medicine, 2011. 155(12): p. 839-849.
9. Bagdasarian, N., K. Rao, and P. N. Malani, *Diagnosis and treatment of Clostridium difficile in adults: a systematic review*. JAMA, 2015. 313(4): p. 398-408.
10. Rao, K. and P. N. Malani, *Diagnosis and Treatment of Clostridioides (Clostridium) difficile Infection in Adults in 2020*. JAMA, 2020. 323(14): p. 1403-1404.
11. Lillehoj, E. P., B. T. Kim, and K. C. Kim, *Identification of Pseudomonas aeruginosa flagellin as an adhesin for Muc1 mucin*. American Journal of Physiology-Lung Cellular and Molecular Physiology, 2002. 282(4): p. L751-L756.
12. Blair, D. F. and S. K. Dutcher, *Flagella in prokaryotes and lower eukaryotes*. Curr Opin Genet Dev, 1992. 2(5): p. 756-67.
13. Homma, M., et al., *Hook-associated proteins essential for flagellar filament formation in Salmonella typhimurium*. J Bacteriol, 1984. 157(1): p. 100-108.
14. Postel, S., et al., *Bacterial flagellar capping proteins adopt diverse oligomeric states*. Elife, 2016. 5.
15. Tasteyre, A., et al., *Role of FliC and FliD flagellar proteins of Clostridium difficile in adherence and gut colonization*. Infect Immun, 2001. 69(12): p. 7937-40.
16. Tasteyre, A., et al., *Molecular characterization of fliD gene encoding flagellar cap and its expression among Clostridium difficile isolates from different serogroups*. Journal of Clinical Microbiology, 2001. 39(3): p. 1178-1183.
17. Dingle, T. C., G. L. Mulvey, and G. D. Armstrong, *Mutagenic Analysis of the Clostridium difficile Flagellar Proteins, FliC and FliD, and Their Contribution to Virulence in Hamsters*. Infection and Immunity, 2011. 79(10): p. 4061-4067.
18. Ghose, C., et al., *Immunogenicity and protective efficacy of recombinant Clostridium difficile flagellar protein FliC*. Emerging Microbes & Infections, 2016. 5: p. 1-10.
19. Karpinski, P., et al., *Motility and the genotype diversity of the flagellin genes fliC and fliD among Clostridioides difficile ribotypes*. Anaerobe, 2022. 73: p. 102476.
20. Tasteyre, A., et al., *Phenotypic and genotypic diversity of the flagellin gene (fliC) among Clostridium difficile isolates from different serogroups*. Journal of Clinical Microbiology, 2000. 38(9): p. 3179-3186.
21. Stevenson, E., N. P. Minton, and S. A. Kuehne, *The role of flagella in Clostridium difficile pathogenicity*. Trends in microbiology, 2015. 23(5): p. 275-282.
22. Yonekura, K., S. Maki-Yonekura, and K. Namba, *Structure analysis of the flagellar cap-filament complex by electron cryomicroscopy and single-particle image analysis*. Journal of Structural Biology, 2001. 133(2-3): p. 246-253.

23. Kutsukake, K., *Excretion of the anti-sigma factor through a flagellar substructure couples flagellar gene expression with flagellar assembly in Salmonella typhimurium.* Molecular and General Genetics MGG, 1994. 243(6): p. 605-612.

24. Malten M, Hollmann R, Deckwer W-D, Jahn D. 2005. *Production and secretion of recombinant Leuconostoc mesenteroides dextransucrase DsrS in Bacillus megaterium.* Biotechnol Bioeng 89:206-218.

25. Yoshino, Y., et al., *Clostridium difficile flagellin stimulates toll-like receptor 5, and toxin B promotes flagellin-induced chemokine production via TLR5.* Life Sci, 2013. 92(3): p. 211-7.

26. Ghose, C., et al., *Toll-like receptor 5-dependent immunogenicity* and *protective efficacy of a recombinant fusion protein vaccine containing the nontoxic domains of Clostridium difficile* toxins *A* and *B* and *Salmonella enterica* serovar *typhimurium flagellin in a mouse model of Clostridium difficile disease.* Infect Immun, 2013. 81(6): p. 2190-6.

27. Batah, J., et al., *Clostridium difficile flagella induce a pro-inflammatory response in intestinal epithelium of mice in cooperation with toxins.* Sci Rep, 2017. 7(1): p. 3256.

28. Jarchum, I., et al., *Toll-like receptor 5 stimulation protects mice from acute Clostridium difficile colitis.* Infect Immun, 2011. 79(4): p. 1498-503.

29. Trzilova, D., et al., *Flagellum* and toxin *phase variation impacts intestinal colonization* and *disease development in a mouse model of Clostridioides difficile infection.* Gut Microbes, 2022. 14(1): p. 2038854.

30. Stabler, R. A., et al., *Comparative genome and phenotypic analysis of Clostridium difficile* 027 strains *provides insight into the evolution of a hypervirulent bacterium.* Genome biology, 2009. 10(9): p. 1-15.

31. Groß, U., et al., *Comparative genome* and *phenotypic analysis of three Clostridioides difficile strains isolated from a single patient provide insight into multiple infection of C. difficile.* BMC genomics, 2018. 19(1): p. 1-14.

32. He, M., et al., *Evolutionary dynamics of Clostridium difficile over short and long time scales.* Proceedings of the National Academy of Sciences, 2010. 107(16): p. 7527-7532.

33. Tasteyre, A., et al., *A Clostridium difficile gene encoding flagellin.* Microbiology, 2000. 146(4): p. 957-966.

34. Sebaihia, M., et al., *The multidrug-resistant human pathogen Clostridium difficile has a highly mobile, mosaic genome.* Nature genetics, 2006. 38(7): p. 779-786.

35. Cairns, M., et al., *Genomic epidemiology of a protracted hospital outbreak caused by a toxin A* negative *Clostridium difficile sublineage PCR ribotype* 017 *strain in London, England.* Journal of clinical microbiology, 2015. 53(10): p. 3141-3147.

36. Riedel, T., et al., *High metabolic versatility of different toxigenic and non-toxigenic Clostridioides difficile isolates.* International Journal of Medical Microbiology, 2017. 307(6): p. 311-320.

37. Chunhui Li, J. H., Duolong Zhu, Xiujuan Meng, Soumyadeep Chakraborty, Celine Harmanus, Shaohui Wang, Zhong Peng, Wiep Klaas Smits, Anhua Wu, Xingmin Sun, *Genomic and phenotypic characterization of a Clostridioides difficile strain of the epidemic ST37 type from China.* 2022.

38. Depitre, C., et al., *Serogroup F strains of Clostridium difficile produce toxin B but not toxin A.* Journal of medical microbiology, 1993. 38(6): p. 434-441.

39. Soehn, F., et al., *Genetic rearrangements in the pathogenicity locus of Clostridium difficile strain 8864-implications for transcription, expression and enzymatic activity of toxins A and B.* Molecular and General Genetics MGG, 1998. 258(3): p. 222-232.

40. Janezic, S., et al., *Comparative genomics of Clostridioides difficile toxinotypes identifies module based toxin gene evolution.* Microbial genomics, 2020. 6(10).

41. Brouwer, M. S., et al., *Draft genome sequence of the nontoxigenic Clostridium difficile strain CD37.* 2012, Am Soc Microbiol.

42. Wang, S., et al., *Genomic and Phenotypic Characterization of the Nontoxigenic Clostridioides difficile Strain CCUG37785 and Demonstration of Its Therapeutic Potential for the Prevention of C. difficile Infection.* Microbiology Spectrum, 2022.10(2): p. e01788-21.

43. Frentrup, M., et al., *A publicly accessible database for genome sequences supports tracing of transmission chains and epidemics.* 2020.

44. Kumar, S., et al., *MEGA X: molecular evolutionary genetics analysis across computing platforms.* Molecular biology and evolution, 2018. 35(6): p. 1547-1549.

45. Zimmermann, L., et al., *A completely reimplemented MPI bioinformatics toolkit with a new HHpred server at its core.* Journal of molecular biology, 2018. 430(15): p. 2237-2243.

46. Gabler, F., et al., *Protein Sequence Analysis Using the MPI Bioinformatics Toolkit.* Current Protocols in Bioinformatics, 2020. 72(1): p. e108.

47. Waterhouse, A. M., et al., *Jalview Version 2—a multiple sequence alignment editor and analysis workbench.* Bioinformatics, 2009. 25(9): p. 1189-1191.

48. Livingstone, C. D. and G. J. Barton, *Protein sequence alignments: a strategy for the hierarchical analysis of residue conservation.* Bioinformatics, 1993. 9(6): p. 745-756.

49. Cartman, S. T., et al., *Precise Manipulation of the Clostridium difficile Chromosome Reveals a Lack of Association between the tcdC Genotype* and Toxin *Production.* Applied and Environmental Microbiology, 2012. 78(13): p. 4683-4690.

50. Wang, Y. K., et al., *A chimeric protein comprising the glucosyltransferase and cysteine proteinase domains of toxin B and the receptor binding domain of toxin A induces protective immunity against Clostridium difficile infection in mice and hamsters.* Hum Vaccin Immunother, 2015. 11(9): p. 2215-22.

51. Perez, J., V. S. Springthorpe, and S. A. Sattar, *Clospore: a liquid medium for producing high titers of semi-purified spores of Clostridium difficile.* J AOAC Int, 2011. 94(2): p. 618-26.

52. Sorg, J. A. and A. L. Sonenshein, *Inhibiting the initiation of Clostridium difficile spore germination using analogs of chenodeoxycholic acid, a bile acid.* J Bacteriol, 2010. 192(19): p. 4983-90.

53. Chen, X., et al., *A mouse model of Clostridium dificile-associated disease.* Gastroenterology, 477 2008. 135(6): p. 1984-92.

54. Joshi, L. T., et al., *Contribution of Spores to the* 478 *Ability of Clostridium difficile To Adhere to Surfaces.* Applied and Environmental Microbiology, 2012. 78(21): p. 7671-7679.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described.

What is claimed is:

1. A fusion protein comprising:

a portion of at least one flagellin protein (FliC) from a Gram-positive bacterium; and a portion of at least one cap protein (FliD) from a Gram-positive bacterium;

wherein the Gram-positive bacterium is from the genus *Clostridioides;* wherein the fusion protein has a sequence of SEQ ID NO: 7.

2. The fusion protein of claim 1, wherein the Gram-positive bacterium is *Clostridioides difficile* (*C. difficile*).

*     *     *     *     *